US006186966B1

United States Patent
Grim et al.

(10) Patent No.: US 6,186,966 B1
(45) Date of Patent: Feb. 13, 2001

(54) HARDENABLE ORTHOPAEDIC SUPPORT WITH IMPROVED CONFIGURATION

(75) Inventors: Tracy E. Grim, Tulsa, OK (US); Joseph M. Iglesias, Thousand Oaks, CA (US); Kelly M. Speakes, Woodland Hills, CA (US); Michael Campos, Granada Hills, CA (US); Steven T. Pelote, Valley Village, CA (US)

(73) Assignee: Royce Medical Co., Camarillo, CA (US)

( * ) Notice: Under 35 U.S.C. 154(b), the term of this patent shall be extended for 0 days.

(21) Appl. No.: 09/307,300

(22) Filed: May 7, 1999

Related U.S. Application Data

(63) Continuation-in-part of application No. 09/088,905, filed on Jun. 2, 1998.

(51) Int. Cl.[7] .................................................. A61F 5/00
(52) U.S. Cl. ................................................ 602/6; 128/878
(58) Field of Search ............................ 602/6, 5; 128/878, 128/879, 881

(56) References Cited

U.S. PATENT DOCUMENTS

| | | |
|---|---|---|
| 4,683,877 | 8/1987 | Ersfeld et al. . |
| 4,770,299 | 9/1988 | Parker . |
| 4,996,979 | * 3/1991 | Grim et al. . |
| 5,166,480 | 11/1992 | Bottger et al. . |
| 5,334,442 | 8/1994 | Okamoto et al. . |
| 5,540,964 | * 7/1996 | Mallen . |
| 5,807,295 | 9/1998 | Hutcheon et al. . |

* cited by examiner

Primary Examiner—Michael A. Brown
Assistant Examiner—Lalita M. Hamilton
(74) Attorney, Agent, or Firm—Oppenheimer Wolff & Donnelly

(57) ABSTRACT

An orthopaedic support assembly is formed of a double-knit type fabric material with spaced interwoven layers formed of high strength materials and an open-work matrix of filaments or threads interconnecting the layers. The fabric preferably includes high strength stiff filaments of fiberglass, carbon fibers, or aramids and thermoplastic material to facilitate heat bonding of cut edges. The fabric is impregnated with a water-hardenable material. The support material or product is packaged in a water-vapor impermeable package; and is opened and water is supplied to the fabric when it is applied to the part of the anatomy requiring support. The fabric may be included in a soft goods support including a water distribution network and straps to hold the support in place. The double-knit type material may be variable in thickness and may be three dimensional in its configuration. An orthopaedic support or splint may have an inner core material of the double-knit type fabric, an impermeable stretch bonded laminate layer on one side, and a microporous plastic layer on the other side to facilitate water activation of the core material.

40 Claims, 18 Drawing Sheets

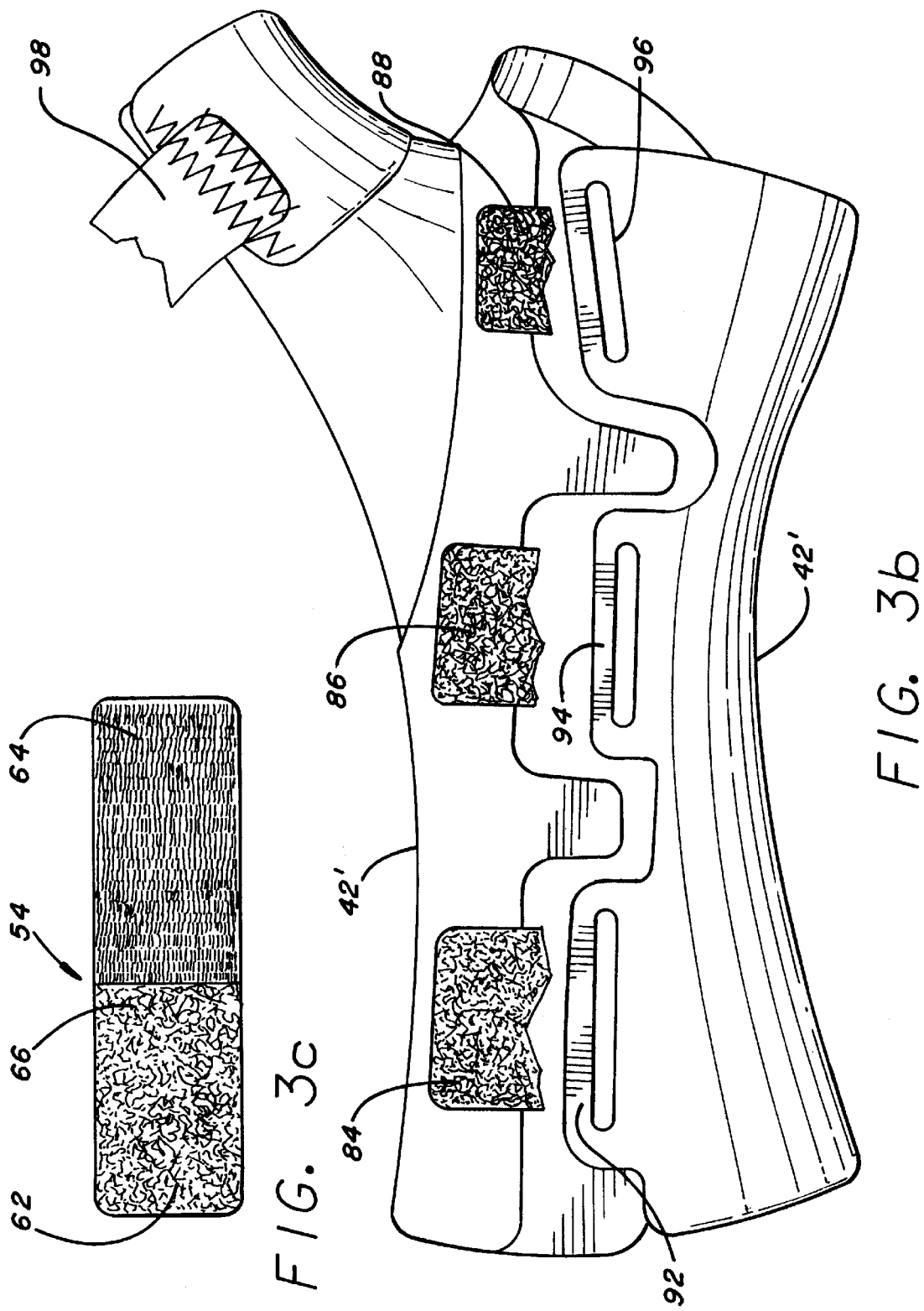

FIG. 15
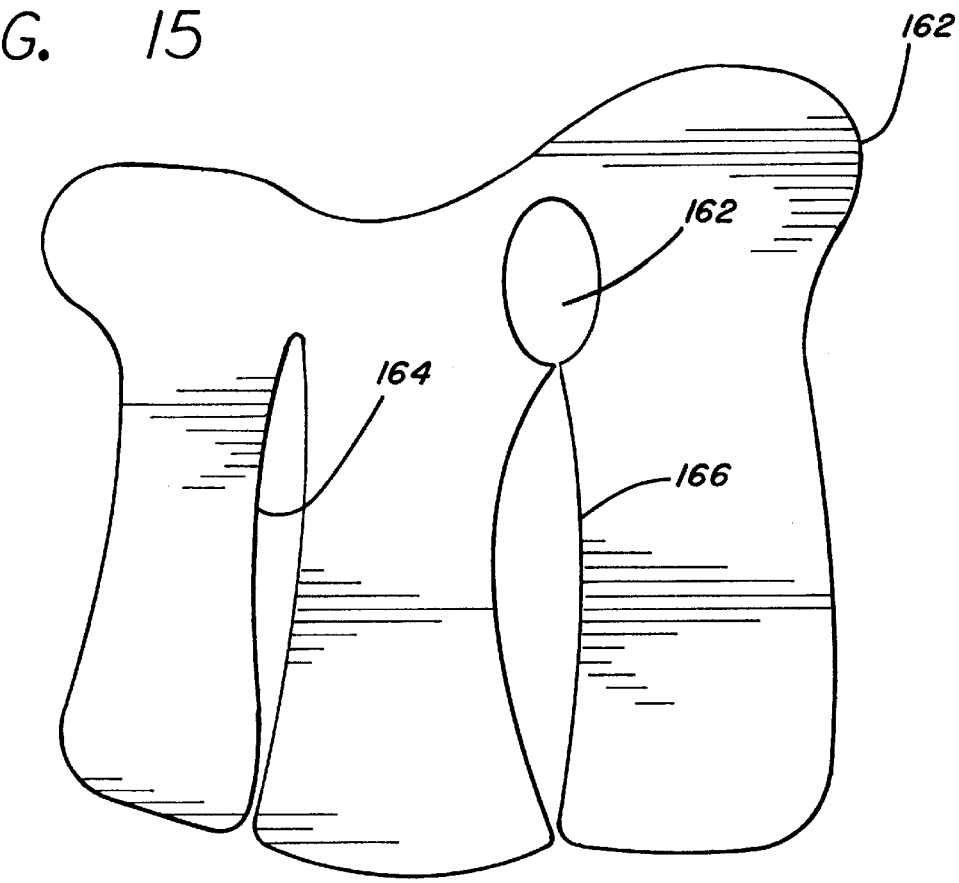
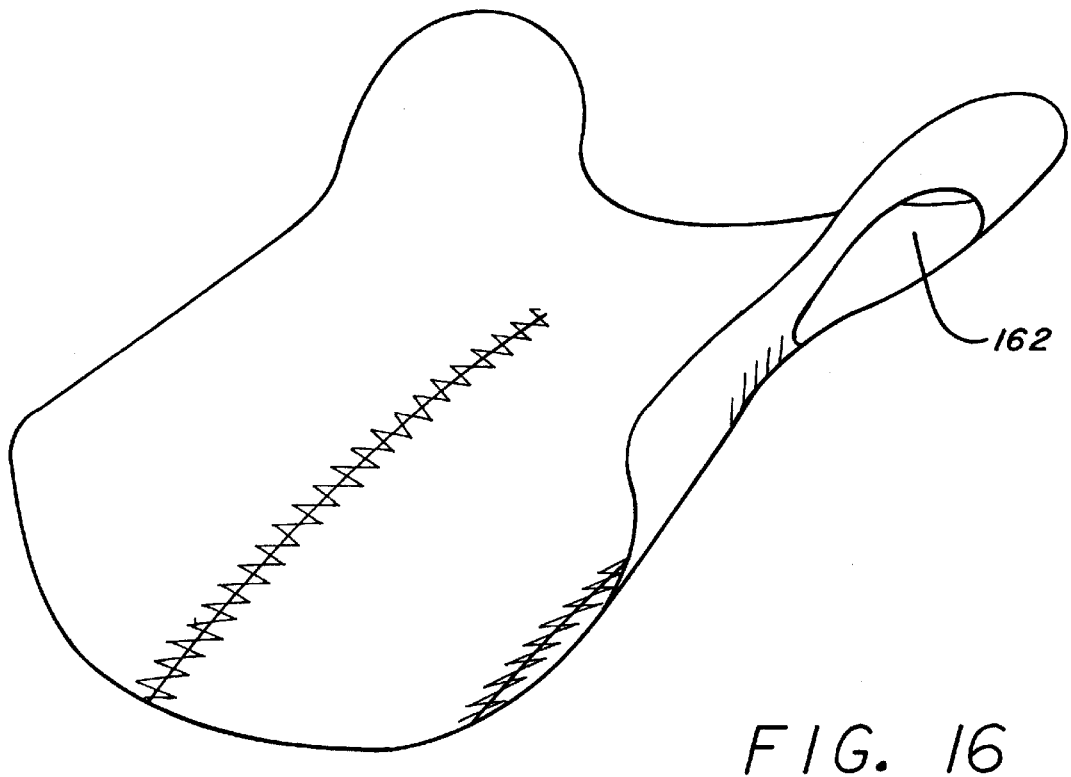
FIG. 16

HARDENABLE ORTHOPAEDIC SUPPORT WITH IMPROVED CONFIGURATION

RELATED PATENT APPLICATIONS

This is a continuation-in-part of U.S. patent application Ser. No. 09/088,905, filed Jun. 2, 1998.

FIELD OF THE INVENTION

This invention relates to improved water-hardenable orthopaedic splints or supports.

BACKGROUND OF THE INVENTION

It has previously been proposed to use water-hardenable materials such as resins in orthopaedic supports and casts; and typical patents disclosing such products include U.S. Pat. No. 4,996,979, granted Mar. 5, 1991, and U.S. Pat. No. 4,683,877, granted Aug. 4, 1987. However, when materials as disclosed in these patents are employed, the flow of liquid through the open cell foam or layers of fabric, as well as the strength of the orthopaedic support may not be subject to the desired level of control.

It is also noted that these prior art products mentioned above have other problems. Thus, for example with regard to the casts or supports using layers of material, care must be taken to firmly engage the layers during the exotherm portion of the setting period to ensure unitary bonding of the entire layered cast or assembly. Doctors practicing in this area even have a saying: "rub it like you love it," to encourage full engagement of the layers during hardening of the water-hardenable material. This step obviously requires care and expertise, as it is undesirable to apply undue force to an injured limb involving a broken limb, for example. Further, if this technique is not properly employed, the layers will not fully bond together, and the cast or support will be weak, and the layers could separate. Also with regard to the hardenable splints or supports using open cell foam, they may lack sufficient flexibility and conformability to properly fit the three-dimensional parts of the anatomy requiring splinting or support.

Flat rigid panels have also been proposed using double-knit fabrics and hardenable resins, as indicated by U.S. Pat. No. 5,166,480, granted Nov. 24, 1992, and entitled "Knitted Fabric Panel Structure and Process of Manufacturing." Reference is also made to U.S. Pat. No. 5,807,295, which discloses double-knit "Medical Articles." This patent includes a cursory disclosure of the use of medical material and water-hardenable material in double-knit material in certain specific simple configurations. Attention is also directed to U.S. Pat. No. 5,334,442, granted Aug. 2, 1994. This patent discloses an intermediate pliant sheet which may be made of a fabric such as glass fiber impregnated with a water-hardenable material. Then, on both sides of this pliant layer, the patentees disclose the use of layers of double-knit material. Thus, with double-knit material present in the assembly, it is not used to receive the water-hardenable material but is only used for padding.

As noted above, prior art orthopaedic products have involved shortcomings in the flow control of water to the water-hardenable material and the strength of the orthopaedic device.

Reference is also made to U.S. Pat. No. 4,770,299 granted Sep. 13, 1988, and entitled "Roll Form Medical Bandaging Product," which discloses a water-hardenable support. This '299 patent discloses a number of overlaid inner layers of fiberglass, which are impregnated with water-hardenable material, and an outer layer of a flexible, non-woven material, to form a protective layer adjacent the skin. This outer layer, which encloses the assembly, is water-permeable to permit wetting of the core which is impregnated with the water-hardenable material. However, this water permeability is somewhat undesirable, as it permits water or moisture to engage the skin, and the exothermic reaction accompanying wetting of the core may result in uncomfortable transmission of heat to the skin.

Concerning another aspect of the current practice of orthopaedic splinting and supporting, with layers of fiberglass being used for the water-hardenable core of the splints or supports, it requires considerable skill and practice to form splints or supports of varying thickness which may be required or which may be desirable for certain applications. Thus, for example, when a cast is to be provided for a foot and lower leg, it may be desirable to have greater thickness in the lower portion of the cast, and a lesser thickness in the vicinity of the shin or the calf of the user. With the present practice of using layers of fiberglass cloth, it requires considerable skill and practice to form a varying thickness layered cast or support which will have proper inter-layer bonding and strength.

Another problem encountered in this field is the fraying of the edges of material when cloth material, such as fiberglass, is cut. In this regard, following curing, the frayed edges may be hardened and may become sharp so that these sharp edges may injure adjacent soft tissue.

SUMMARY OF THE INVENTION

Objects of the present invention include overcoming the shortcomings of prior art arrangements of the type discussed hereinabove.

Accordingly, one object of the present invention is to improve both the control of the flow of water to the curable resin in orthopaedic supports or splints, and concurrently to provide the desired strength for the product.

Additional objects include increasing the reliability and simplifying the application, increasing conformity, reducing the thickness and weight while increasing the strength of casting materials.

In accordance with a method for forming an orthopaedic support illustrating the principles of the invention, an integral double layer fabric with a central open-work matrix, such as a double-knit material, is impregnated with a water-hardenable material under low humidity conditions, and is packaged in a water-vapor impermeable package. The impregnated double-knit type material is located adjacent the injured portion of the anatomy, such as a broken bone, so that the material conforms to the desired configuration of the injured part of the anatomy. Water is applied through the open-work matrix of the double-knit material to rapidly wet the water-hardenable material, to cause stiffening of the orthopaedic support and preventing undesired movement of the injured part. Water is applied to the double-knit type material prior to application to the anatomy in the case of tapes and flat splinting shapes; and in the case of soft goods type products, following application of the soft goods support to the anatomy.

The double-knit type material preferably includes fiberglass or other high strength fibers such as aramids or carbon fibers to provide the desired high strength and stiffness. These high strength fibers are relatively stiff and do not easily bend sharply without breaking, and accordingly are not normally employed in double-knit structures which are normally fairly tightly woven and have fibers which are bent sharply in the complex knit and inter-connection patterns. Thus, for example, in the U.S. Pat. No. 5,807,295 cited hereinabove, the fibers or filaments as mentioned in Col. 3, lines 20 to 36, are of the more flexible type, not the higher strength, stiffer filaments discussed above. To permit the unexpected use of the high strength filaments in double-knit assemblies illustrating the principles of this invention, applicants employ a double-knit weave which is looser than normal so that unduly sharp bends of the filaments do not occur. In addition, suitable arrangements are provided for avoiding fraying at the edges of the fabric. This may be accomplished by providing closed knit configurations at the edges or by incorporating thermoplastic material into the assembly for melting and concurrently bonding the edges where they are cut, or other comparable techniques. Further, to avoid injury to the skin of a patient by the sharp edges or ends associated with high strength fibers, suitable high strength but soft padding material may be used; and this padding may be waterproof to avoid exposure of the skin to the exothermic reaction when the water-hardenable material is exposed to water.

As noted above, a relatively loose double-knit weave is preferably used to accommodate the relatively stiff fibers which may be employed. When discussing Raschel knit fabrics, the fabric courses includes "picks" in one direction and "wales" in the other direction. In one preferred fabric, the number of picks per inch was 23, and the number of wales per inch was 14½. A specific range of 18 to 28 and a broader range of 10 to 30 picks per inch may be employed; and a specific range of 10 to 20, and a broader range of 5 to 25 wales per inch are contemplated.

In one preferred fabric, the upper and lower layers of the double-knit type material were formed of fiberglass, and the open matrix of interconnecting fibers was formed of 30 denier polyester monofilament, a thermoplastic material. The fiberglass constituted 71% by weight of the assembly, and the polyester was 29%. Using this type of assembly, with stiff high strength material and a thermoplastic material, the double-knit type material may be concurrently cut and heat applied to melt and fuse the thermoplastic into the fiberglass, thereby preventing fraying or unraveling of the cut edges. Ultrasonic cutting and sealing equipment to accomplish the foregoing is available, for example, from Branson Ultrasonics Corp., 41 Eagle Road, Danbury, Conn. 06813-1961. More generally, the amount of the fiberglass or other stiff high strength filaments may range from 10% to 100% by weight of the double-knit fabric, with from 20% to 80% being preferred. The remainder may be of any desired filaments to suit the application, with a thermoplastic being preferred to permit cut edge treatment as described above.

Incidentally, the double-knit type material mentioned above normally includes two spaced interwoven or knit layers and an open-work matrix of fibers or yarns interconnecting the two layers.

The orthopaedic support preferably includes high strength material such as glass fiber fabric, aramids including kevlar fibers, carbon fibers, or other high strength fibers, to provide strength to complement the rigidity or stiffness of the water-hardenable material. One or both of the outer knit or woven layers of the double-knit type material may be formed of fiberglass, or other high strength fibers, and some or all of the fibers or yarns interconnecting the two layers may be of such materials. The high strength fibers have tensile strength above 500 MPa (Megapascals, or kilonewtons per square meter) and preferably above 1,000 MPa.

The orthopaedic support using the double-knit type fabric with its open-work central matrix may take a number of forms, including a tape, a flat or contoured splint shape configured to fit an injured portion of the anatomy, or a soft goods product having straps to secure the support in place, and having the double-knit fabric within its construction.

Regarding the soft goods type support, it may be similar to that showing in U.S. Pat. No. 4,996,979, and may include either a single layer of impregnated double-knit type fabric, or a plurality of such layers, with one or more intermediate water distribution networks. In addition, the soft goods support may include one or more of the following additional features: (1) an outer semi-flexible or semi-rigid member of plastic or the like to provide a general shape to the assembly prior to hardening of the material; (2) water impermeable layers for confining the water; (3) soft cloth lining material for engaging the skin of the injured party; and (4) straps for holding the assembly onto the injured part of the anatomy.

Incidentally, regarding water-hardenable materials and other matters, the disclosure of U.S. Pat. No. 4,996,979 is hereby incorporated into this specification by reference.

Concerning water-vapor impermeable material for packaging the products, metallized mylar or aluminum foil with coatings of plastic on both sides may be employed, in addition to other known barrier materials.

Regarding the flat or contoured blanks to be used as a splint or a support, they may have cut-outs and darts to more closely fit the portion of the anatomy, such as the forearm, wrist and thumb, or elbow, to which they are to be mounted.

Concerning advantages of the invention, it is noted that a single layer of the double-knit material has superior properties to the conventional layers of fiberglass fabric; and it is more stretchable than the fiberglass/foam laminate constructions for orthopaedic casting products which have been proposed heretofore. It also is lighter, thinner and stronger than conventional casting materials.

As an additional advantage of the invention, the application of splints or supports using double-knit type material does not require the special expertise and careful rubbing technique needed to produce a strong layered splint or support. Further, the fact that the inner layer and the outer layer of the double-knit type support material are relatively easily moveable with respect to one another, as they are only coupled by the spacer yarns, means that the material more easily conforms closely to the three-dimensional configuration of the anatomy without wrinkling or undue distortion. Also, cast alterations following hardening are easier to accomplish with no residual sharp edges.

It is further noted that hardenable casts and splints formed of appropriate double-knit type material have higher strength than the prior art foam or multi-layer hardenable splints of comparable thickness and/or weight.

Another accomplishment of one embodiment of the invention involves the provision of an orthopaedic splint or support which has an inner core preferably of double-knit type material, and two different outer layers on its outer surfaces. On one surface, to be located adjacent the skin, is a layer of water resistant or water impermeable padding material such as "SBL" or "Stretch Bonded Laminate" material; and on the other side is a thin flexible porous plastic layer, preferably having micropores, or very tiny holes which may be tapered opening toward the inner core. The SBL material may be formed of two thin layers of non-woven material bonded together with a water resistant adhesive, so that the SBL layer is substantially water impermeable. In order to permit the ready access by water to the inner water-hardenable material in the core, the micropore plastic layer is readily penetrated by water, while the tapered openings pointing inward limit outward flow of the water. Accordingly, the advantages of using comfortable padding on one side which is preferably at least relatively impermeable so that it does not permit flow of water toward the skin, and still permitting easy wetting of the core, are accomplished by the use of the two different materials on the two sides of the assembly. Incidentally, SBL material is available from Kimberly Clark, 1400 Holcom Bridge Road, Roswell, Ga. 90076-2199. While SBL material is preferred, other padding material could be used, with water resistant or water impermeable padding being preferred but not essential.

In order to facilitate penetration by water, the double-knit type material may have an outer layer which is relatively easily penetrated by water with a looser knit or with physical openings in the knit pattern, while the inner layer to be closer to the skin has a tighter weave or surface knit. Further, a water attracting layer such as a hydrophilic material or a "super soaker" material may be located adjacent the lower or inner side of the double-knit type material to encourage full penetration of water. The splint or cast or support material would then have an inner layer of water resistant material such as SBL, a hydrophilic layer, the double-knit type fabric impregnated with water hardenable material, and an optional outer perforated layer through which water may be applied.

Now, regarding varying thickness and elimination of fraying problems, in hardenable orthopaedic splints and supports, it has been determined that double-knit-type material can be formed which has both variable thickness and also has a closed knit fabric configuration which does not have to be cut at the edges or around openings in the fabric. In addition, the orthopaedic basic splint or cast construction does not have to be flat, but may be knit or woven in a three-dimensional configuration which matches the shape of the portion of the anatomy to be supported, thus avoiding folds or wrinkles which might be incident to mounting a flat blank on an ankle or the like. Thus double-knit type fabrics of varying thickness and formed of a particular macro-configuration and size may be constructed with one area relatively thin and other areas relatively thick, and with a completely closed knit configuration. In this regard, the company which makes fabrication machines capable of forming these types of fabrics is H. Stoll GmbH & Co. of Stollweg 1, D-72760 Reutlinger, Germany.

These orthopaedic splint or support blanks may thereafter be impregnated with water-hardenable material and stored in sealed water vapor impermeable packaging until needed.

It is further noted that fraying may be controlled by ultrasonically sealing or thermal bonding of either supplemental plastic material, or of lower melting point fibers or yarns included in the core fabric used in the casting or supporting assembly.

Other objects, features and advantages of the invention will become apparent from a consideration of the following detailed description, and from the accompanying drawings.

BRIEF DESCRIPTION OF THE DRAWINGS

FIG. 3B is a view of an alternative fiberglass soft goods device illustrating the principles of the invention;

FIG. 3C shows a strap using hook and loop type material, which may be employed in the orthopaedic soft goods products of FIGS. 3A and 3B;

FIG. 3D is a schematic side view, showing how the straps hold the soft goods product in place;

FIGS. 15 and 16 show a flat wrist brace with die cuts, and a corresponding wrist brace in a three-dimensional configuration, respectively;

DESCRIPTION OF PREFERRED EMBODIMENTS OF THE INVENTION

Figure 1:
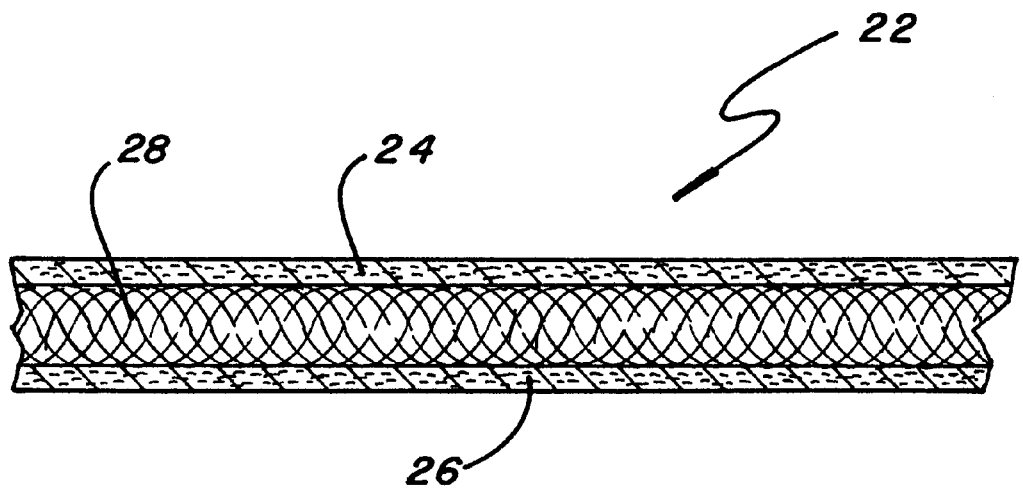
FIG. 1 is a cross-sectional view of a double-knit type material which is to be employed in the fabrication of orthopaedic splints or supports in accordance with the present invention.

Referring more particularly to the drawings, FIG. 1 shows a double-knit fabric 22 including the surface knits 24 and 26 and spacer yarns 28. The surface knits 24 and 26 can be of the same or different knit patterns. These patterns can range anywhere from smooth, essentially continuous surfaces to meshes and other more complex knits. They may be knit from materials such as polyester, nylon, and various high strength fibers, including fiberglass, aramid and/or carbon fibers. The spacer yarns 28 keep the surface knits a specific distance apart, and allow for individual surface movement. They are usually composed of monofilament yarns, but can also be of multi-filament yarns. The spacer yarns 28 typically are made from polyester, nylon, or other thermoplastic materials that can be drawn into a yarn of the desired diameter. In addition, they may be made from glass and other aramid fibers.

Figure 2:
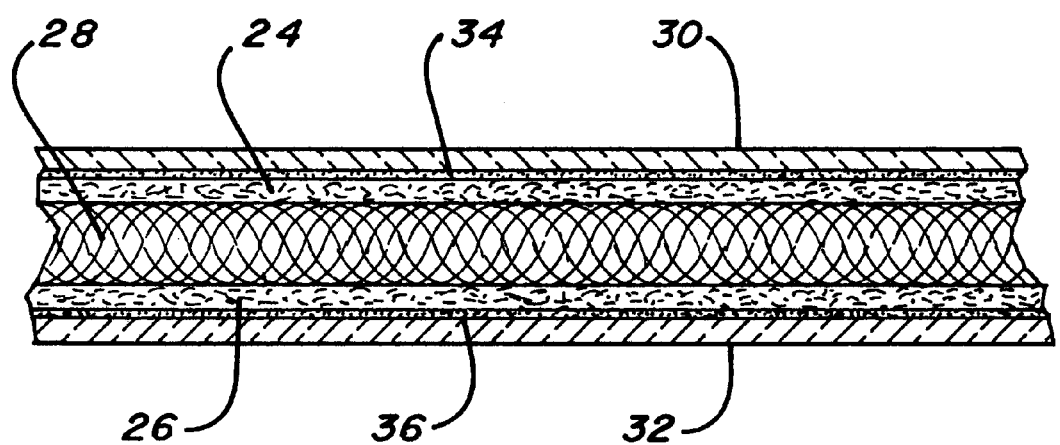
FIG. 2 is a cross-sectional view of a central layer of double-knit material reinforced by layers of high strength material such as fiberglass fabric on both sides of the double-knit material.

FIG. 2 shows how double-knit materials may be reinforced with glass knits or other high strength fabrics to increase their strength. More specifically, fiberglass cloth material 30 and 32 may be bonded to the double-knit material by adhesive webs 34 and 36. This bonding could also be achieved by any other known technique such as by flame bonding, or by sewing, for specific examples. The lamination of the glass knit fabrics 30 and 32 to the double-knit material by the adhesive layers 34 and 36 also reduces the fraying of the glass knit when the assembly is cut, and holds the entire assembly intact during subsequent operations.

In accordance with the present invention, the double-knit type material is impregnated with a water-hardenable material, such as unpolymerized urethane material. These water-hardenable materials are well known, and have been used heretofore in orthopaedic devices. Reference is again made to U.S. Pat. No. 4,996,979, granted Mar. 5, 1991, for detailed information regarding one type of water-hardenable material which may be employed.

One aspect of the present invention, as mentioned above, is the recognition that double-knit material, with its central open-work matrix formed by the spacer yarns, is ideally suited to initially receive the hardenable urethane chemistry, and subsequently to receive the water activation which serves to initiate the hardening and polymerization of the urethane material. Thus, in the various embodiments to be described hereinbelow, the double-knit type material is initially impregnated with a water-hardenable compound, and the orthopaedic device or material is mounted adjacent the portion of the anatomy to be supported, and is hardened in place to conform to the configuration of the anatomy.

Figure 3A:
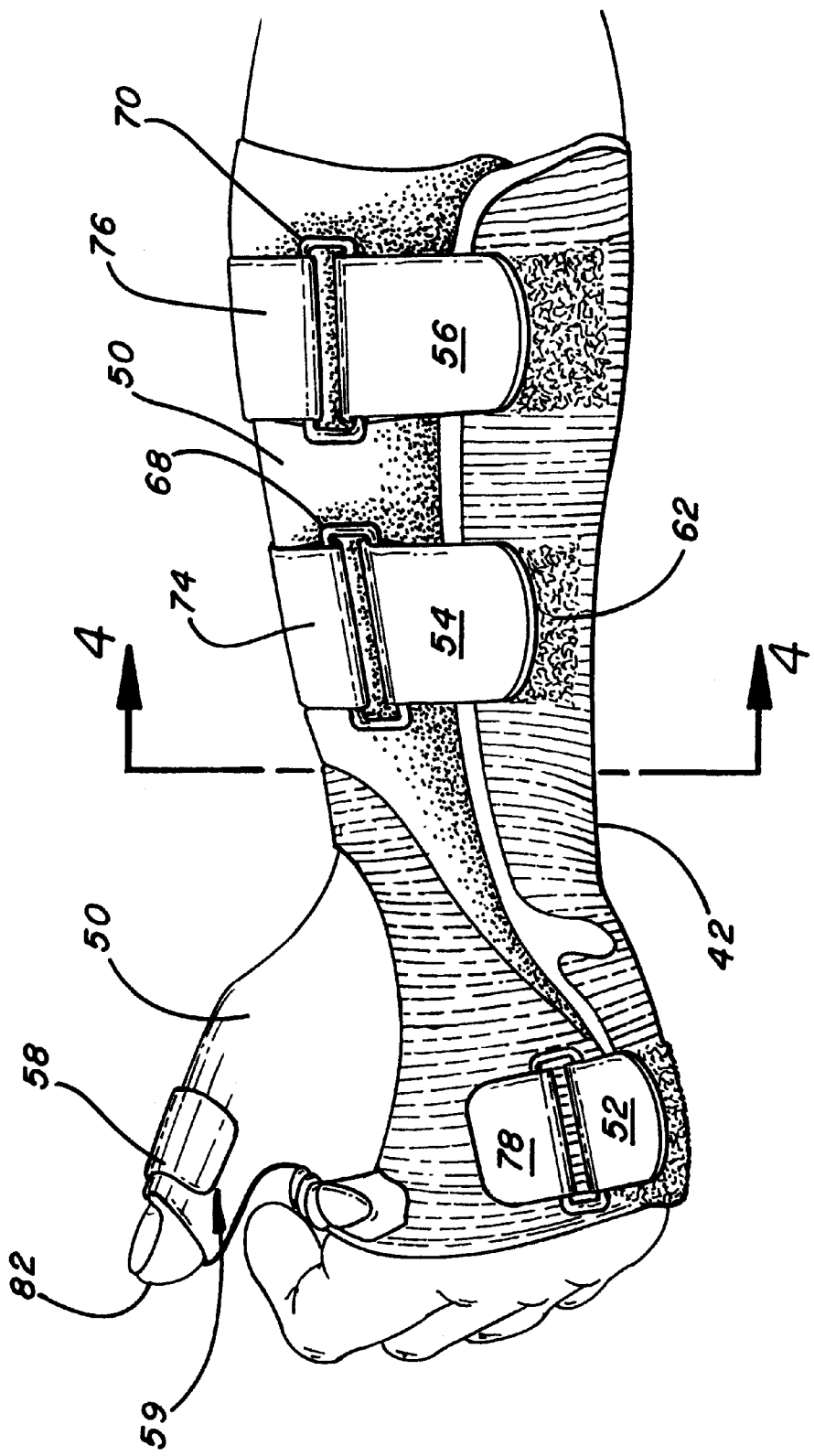
FIG. 3A is a side view of a fiberglass soft goods assembly for the forearm and wrist, employing a double-knit fabric of the type shown in FIGS. 1 and 2.
Figure 4:
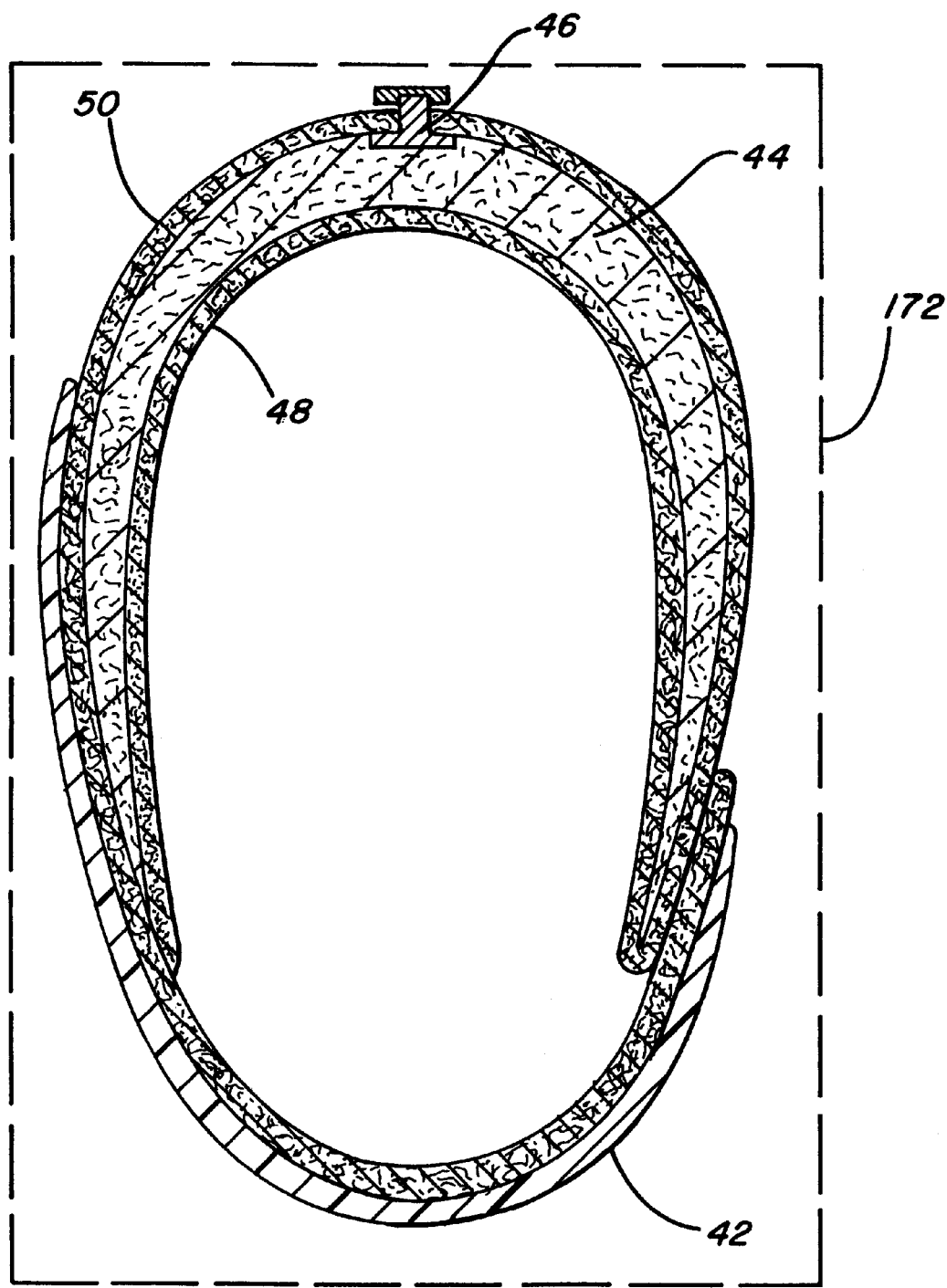
FIG. 4 is a cross-sectional view taken along lines 4—4 of FIG. 3A.

Reference will now be made to FIGS. 3A, 3B, and 3C, and FIG. 4 which is a cross-section taken along lines 4—4 of FIG. 3A. In FIGS. 3A, 3B, and FIG. 4, there is shown a shell-shaped or channel-shaped lower plastic member 42 which may be made of any semi-flexible or semi-rigid plastic material, such as polypropylene, about 1/16-inch in thickness. Mounted on the plastic channel member 42 is a layer of the double-knit material assembly 44, 48, 50 which is impregnated with a water-hardenable urethane material. An inlet construction 46 is provided for receiving a standard or measured amount of water, in order to penetrate and activate the hardening of the urethane material in the double-knit material 44. This can be provided by the use of a syringe having a needle which is inserted through the entry port 46. The inner layer 48 and the outer layer 50 of the assembly include both a water impermeable layer immediately adjacent the double-knit material, and also a layer of cloth for comfortable engagement with the skin of the user and for providing a convenient surface for manipulating the orthopaedic support on its outer surface.

In addition to the materials mentioned in connection with FIG. 4 of the drawings, FIG. 3A shows four straps 52, 54, 56 and 58 which are employed to secure the orthopaedic device onto the forearm of the patient. These strap arrangements may extend from one edge of the channel member 42, to its other edge. The three straps 52, 54, and 56 have a configuration as indicated in FIG. 3C of the drawings. More specifically, strap 54, as shown in FIG. 3C of the drawings, includes a strip of loop type material 62 which is stitched together with a strip of hook type material 64. This type of hook and loop securing material is well known and is commonly sold under the trademark "VELCRO." The two straps may be held together in any desired manner by bonding or by the stitches 66, for specific example, as shown in FIG. 3C. In practice, referring back to FIG. 3A, one portion 62 having loop type material on its outer surface may be secured to the member 42 by adhesive or the like, and the free end 64 of the strap 54 extends up through the rectangular loop 68, and then back over the plastic member 42 to engage the hook type material on the lower surface of the strap 54 with the loop type material 62 of the strap. Incidentally, the rectangular loops 68, 70 and 72 are mounted on loops of the strap members 74, 76 and 78 which may be secured to the other edge (not shown) of member 42. Incidentally, the strap 58 has a simpler configuration and merely holds two portions of the layered material 50 together to provide proper support for the thumb 82 of the patient. The strap 58 and a matching area 59 on material 50 may be provided with mating hook and loop type material to adjustably maintain the strap in the desired closed position to restrain the thumb against excessive movement.

The embodiment of FIG. 3B is similar to that of FIG. 3A, and includes the plastic channel member 42' providing initial support, and the multi-layer material including the double-knit central core, as indicated by the reference numeral 50 showing the outer surface of this multi-layer assembly. In the arrangements of FIG. 3B, the straps 84, 86 and 88 are shown broken away, but in use would extend through the integral loops 92, 94 and 96, respectively. The straps 84, 86 and 88 may be of the same type shown in FIG. 3C with exposed loop type material being secured to the plastic channel member 42', and the portion of the strap extending through the integral loops having mating hook type material on its surface. The strap 98, which is also shown broken away, serves to hold the thumb portion of the brace in its proper position to support the injured thumb and/or forearm of the user.

It is further noted in passing that the double-knit type material as described herein may be substituted for the material shown at reference numeral 24 in FIG. 4 of U.S. Pat. No. 4,996,979, as cited hereinabove.

Figure 5:
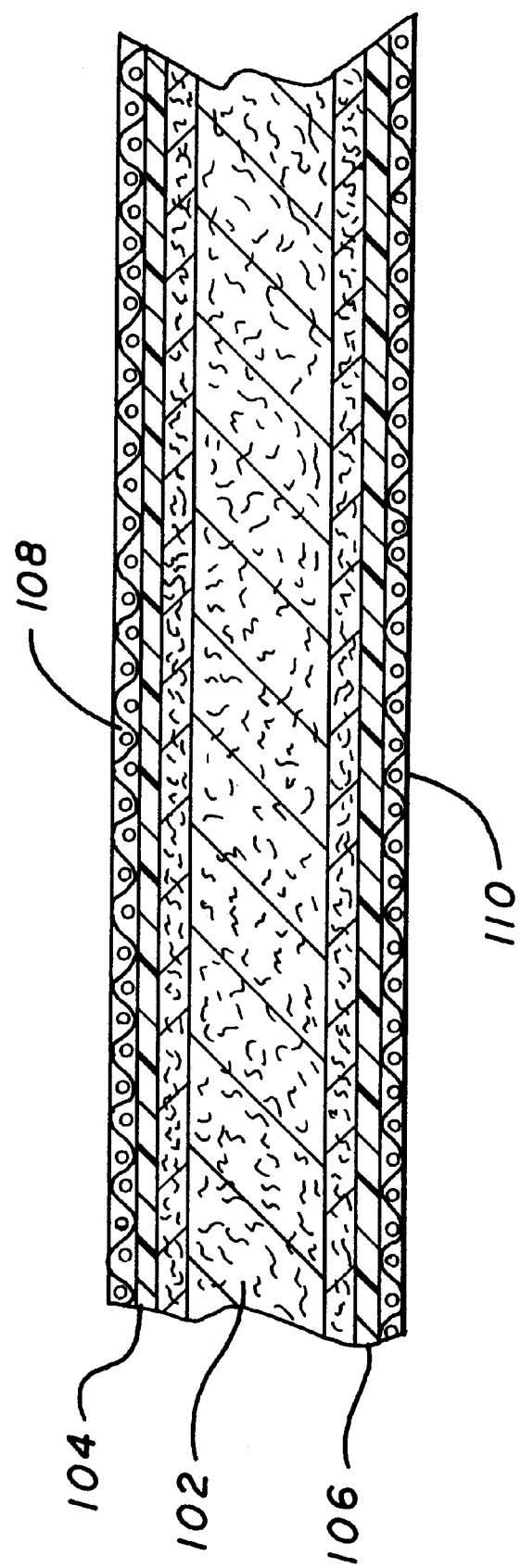
FIG. 5 is a cross-sectional view of an assembly including double-knit material in the center, layers of water impermeable plastic, and finally an outer layer of cloth, which may be employed in the implementation of the present invention.

In the showing of FIG. 5, a central body of double-knit material 102, with two outer surface knits, and a central matrix of spacer yarns is provided with an upper water impermeable plastic layer 104 and a lower water impermeable plastic layer 106 to retain water which is provided to the double-knit material 102 and prevent it from contacting the user, as well as confining the water action to the hardening of the impregnated material. In addition, outer cloth or fabric layers 108 on one side and 110 on the other side are provided for ease in handling the layered material and for comfort in engaging the skin of the user or patient.

Figure 6:
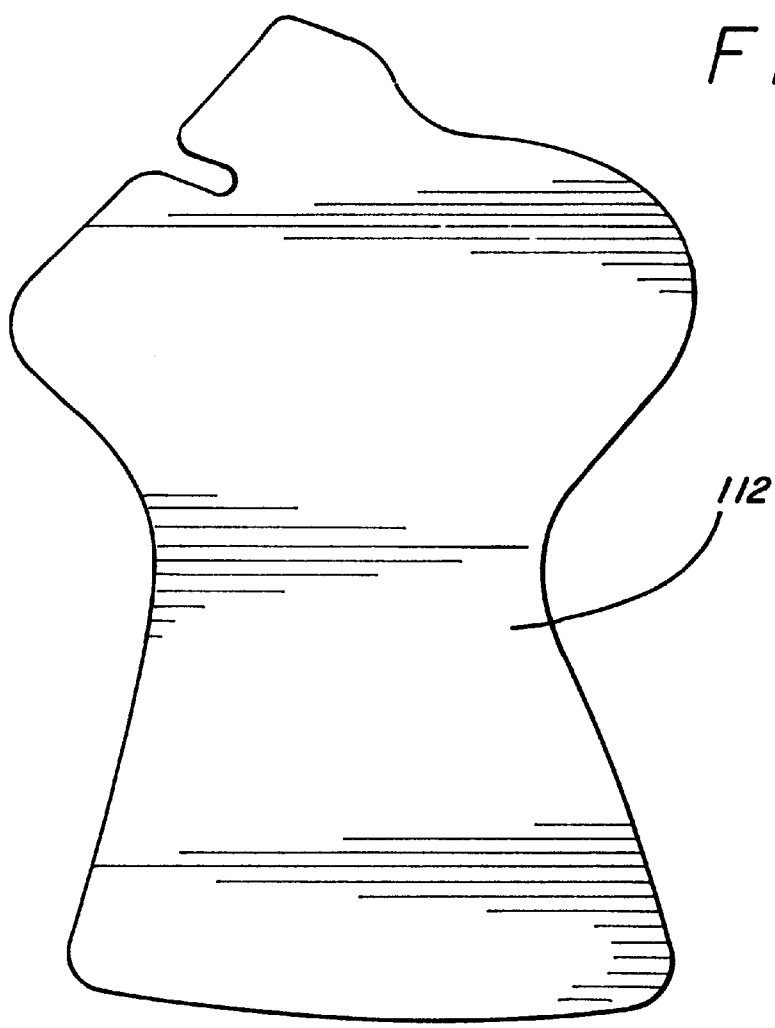
FIG. 6 shows a flat blank formed of the double-knit material of the type shown in FIGS. 1 and 2.
Figure 7:
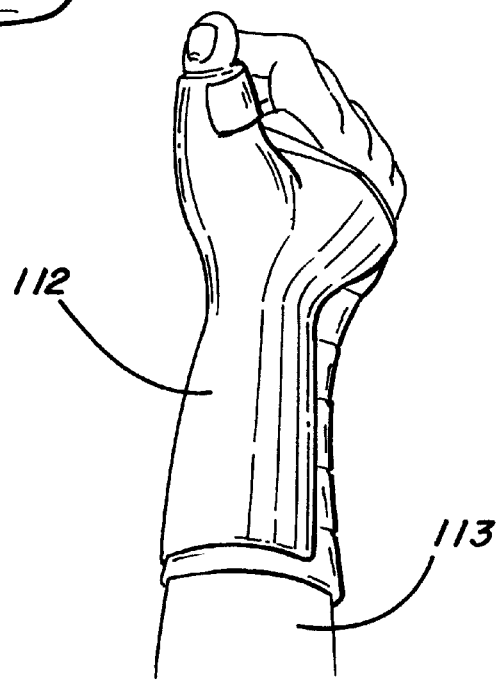
FIG. 7 shows the blank of FIG. 6 mounted on the forearm of a patient to provide supplemental support or splinting of this portion of the anatomy.

FIGS. 6 and 7 show, respectively, a blank 112 for providing splinting or casting action for the forearm 113 of a patient, and the blank 112 being mounted on the forearm 113. The blank 112 as shown in FIG. 6 is specifically configured to be mounted on the forearm, and may be held in place by appropriate elastic tape, or tape provided with hook and loop surfaces, for specific examples, once it is applied to the forearm of the patient. Of course, the blank is formed of the impregnated double-knit material of one of the types described in the present specification, and is initially packaged in a water impermeable package.

Figure 8:
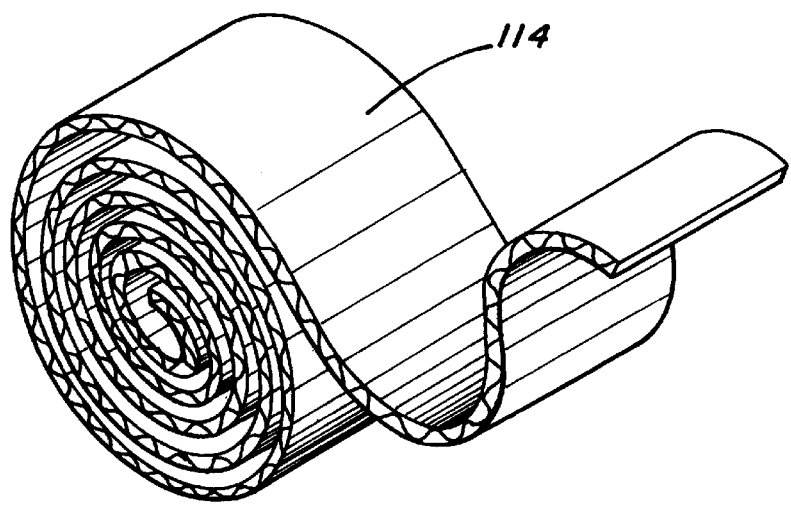
FIG. 8 is a perspective view of an orthopaedic casting tape formed of double-knit material.
Figure 9:
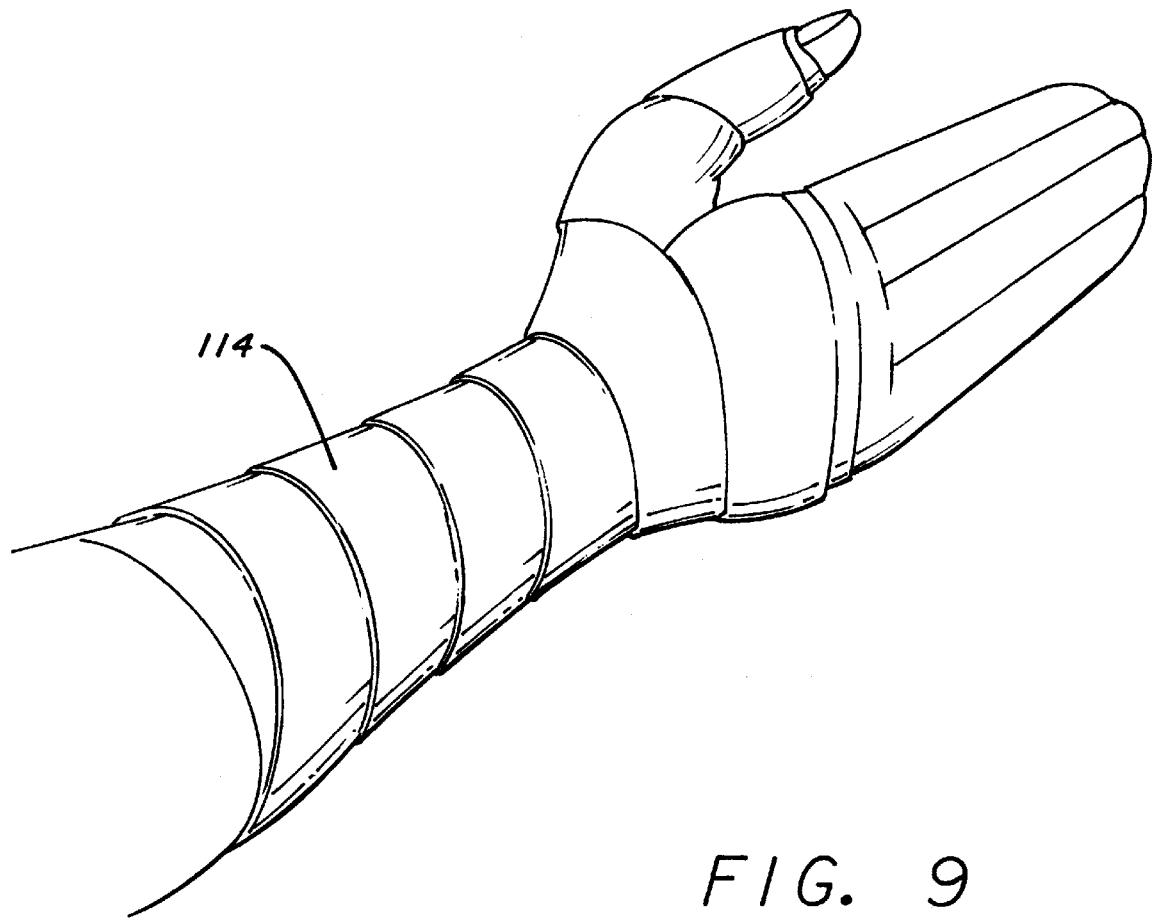
FIG. 9 shows the tape of FIG. 8 mounted on the forearm of a patient to provide casting or supplemental support.

FIG. 8 shows a tape 114 formed of impregnated double-knit material; wound on a hollow core 119; and FIG. 9 shows the tape of FIG. 8 applied to the forearm of a patient for splinting or support purposes.

Figure 10:
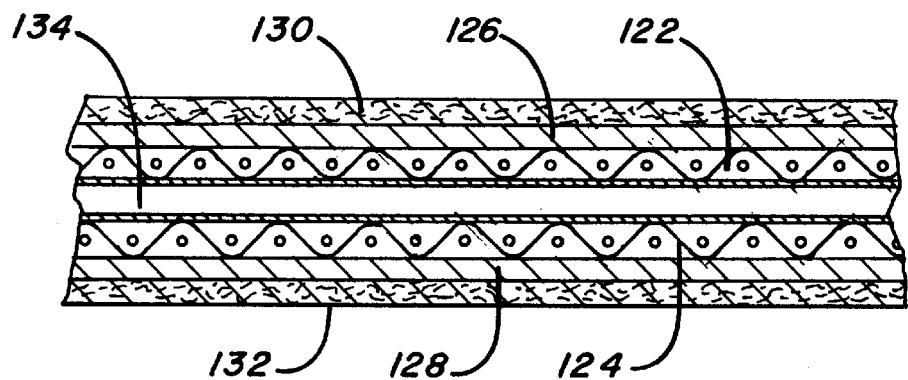
FIG. 10 is a cross-sectional view of a multi-layer construction involving two layers of double-knit material, a central water distribution network, outer water impermeable layers, and cloth fabric on the outside of the assembly.
Figure 11:
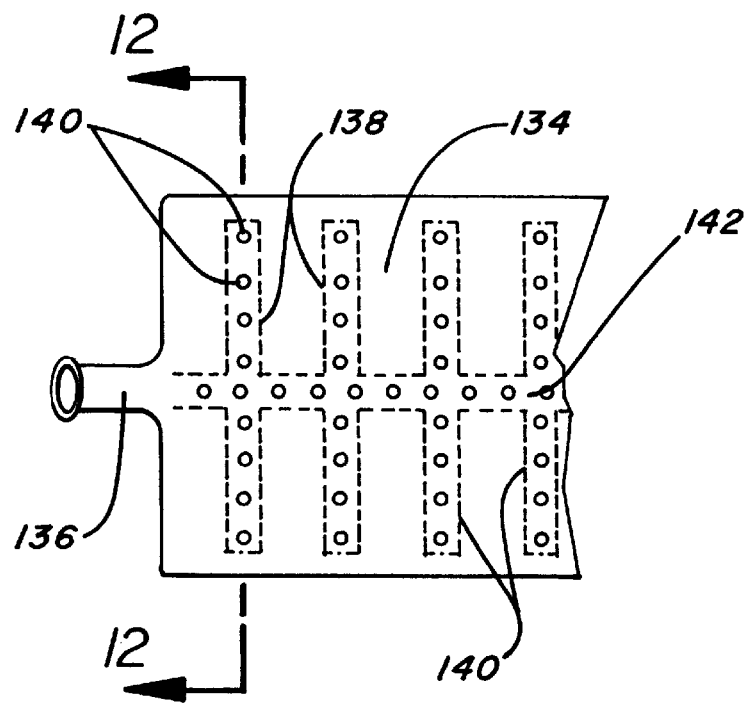
FIG. 11 is a schematic view of a water distribution network included as a central portion of the assembly of FIG. 10.
Figure 12:
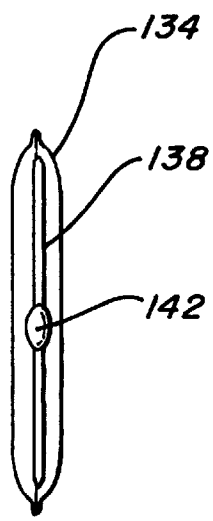
FIG. 12 is a cross-sectional view taken along lines 12—12 of FIG. 11.

FIGS. 10 through 12 show an alternative type of layering which may be employed, for example, in the fiberglass soft goods device of FIGS. 3 and 4. More specifically, the arrangement of FIG. 10 includes two layers of double-knit material designated 122 and 124, an outer water impermeable layer 126 on one side of the assembly, and a water impermeable layer 128 on the other side, with outer fabric layers 130 and 132. A water distribution channel or network 134 is provided to direct activation water into the two impregnated double-knit fabric layers 122 and 124.

FIGS. 11 and 12 show additional views of this water distribution network 134, with an inlet 136 which may be provided with a suitable one-way flapper type valve of a type known in this field, and distribution channels 138 with openings 140 for directing water throughout the two impregnated double-knit fabric layers. FIG. 12 is a cross-sectional view of the thin walled water distribution network, with a central channel 142 and the branch channels 138.

Figures 13, 14:
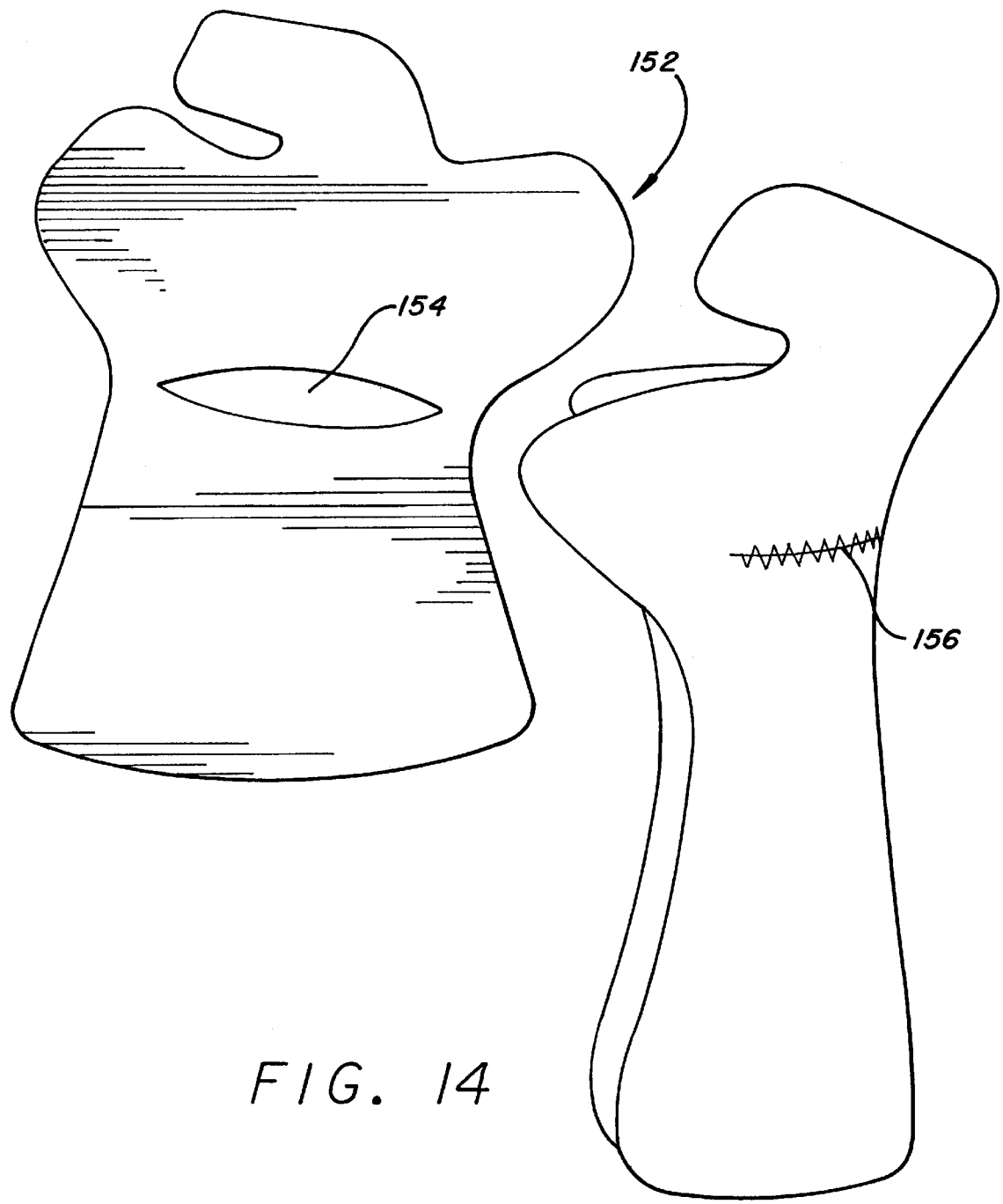
FIG. 13 is a flat blank including a cutout area to help in forming the blank into a cast or support for the thumb.
FIG. 14 shows the blank of FIG. 13 formed into a three-dimensional configuration for application to the forearm and thumb of a patient.

FIG. 13 shows an alternative thumb-spica blank 152 with a die cut opening 154 extending through the thumb-spica blank. The opening 154 may be sewn up, as indicated in FIG. 14 by the stitches 156, or it may be left unstitched if desired. This provision of the opening is of assistance in forming the thumb-spica into its desired and necessary three-dimensional configuration as it is applied to the forearm of the patient, and avoids wrinkling or bunching up of the support blank.

The wrist brace of FIG. 15 is similarly provided with die cut openings or slits 162, 164, and 166. Following stitching or otherwise bonding of the adjacent edges together, the wrist brace is formed into a three-dimensional configuration, as shown in FIG. 16. The opening 162 is to receive the thumb of the patient to assist in locating the wrist brace on the forearm.

Figure 17:
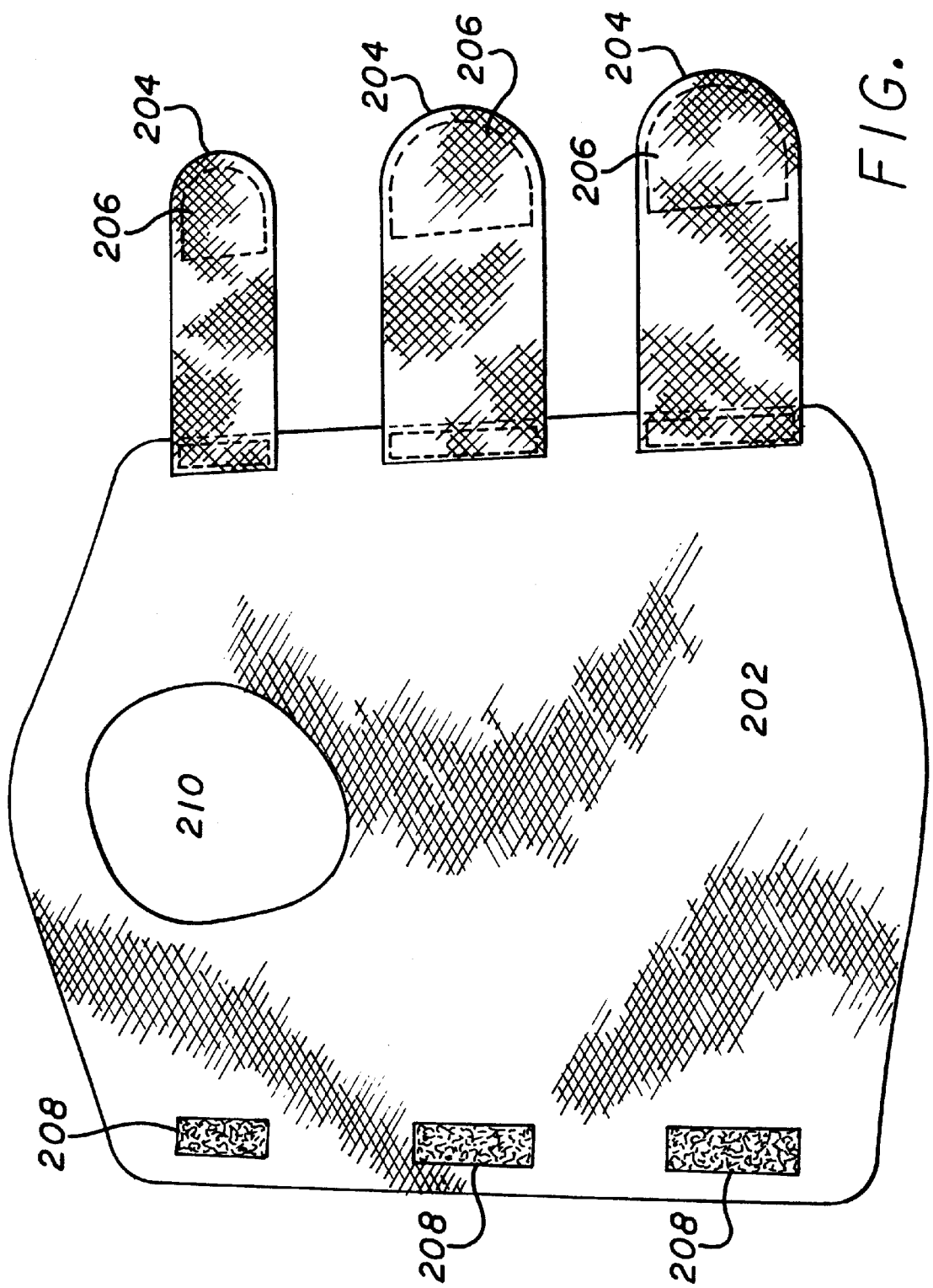
FIG. 17 shows a blank formed of double-knit type material provided with straps.
Figure 18:
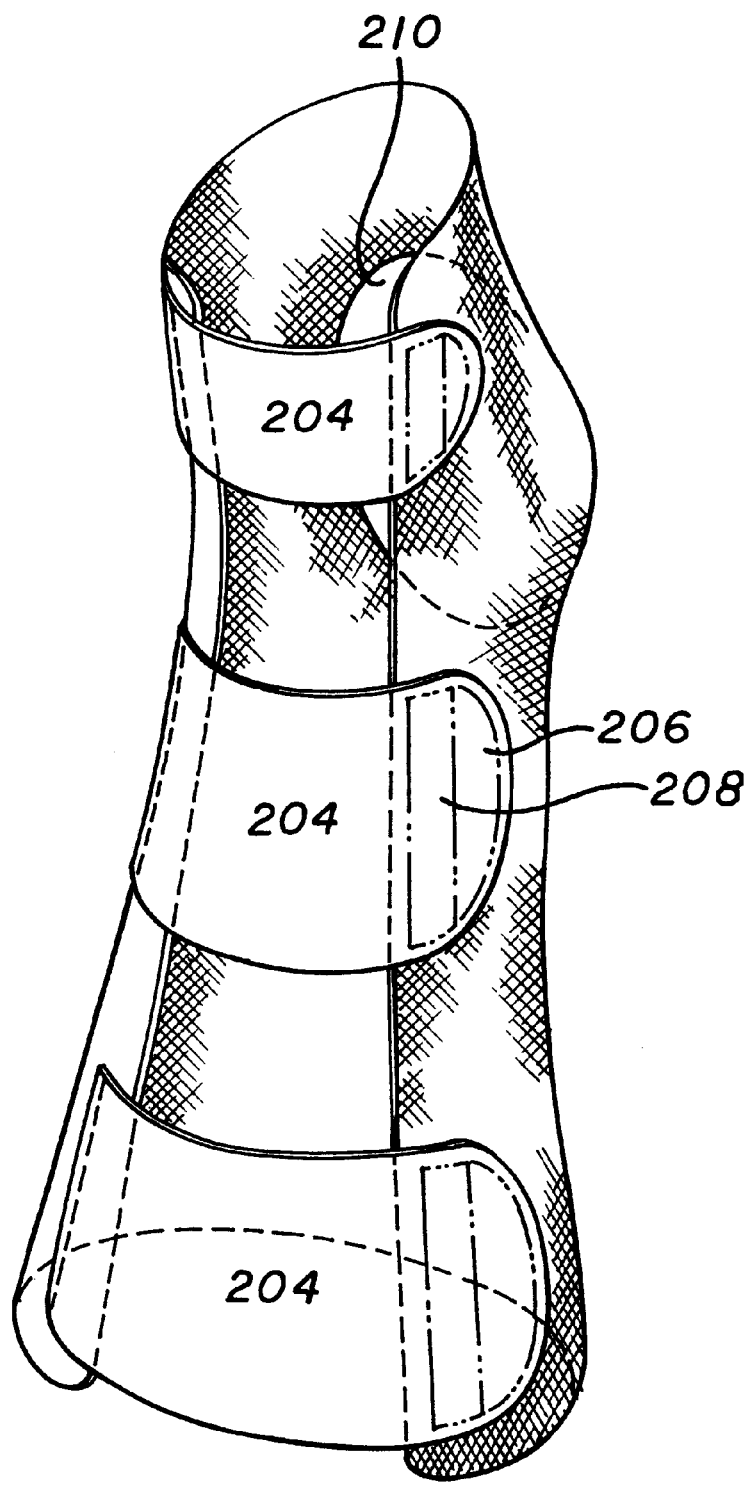
FIG. 18 shows the support or splint of FIG. 17 formed into a three-dimensional configuration.

FIG. 17 shows a flat blank 202 of double-knit-type material, with straps 204 for securing the resultant splint or support in a three-dimensional configuration onto the wrist or forearm of the patient. The double-knit-type material is impregnated with water-hardenable material, and sold in a water vapor impermeable package. At the time of use, it is immersed in water to initiate the hardening, and mounted on the patient, with the pads 206 on the straps mating with pads 208 on the double-knit-type material 202. The pads may be formed of mating hook and loop-type material, known as VELCRO®. The thumb of the patient extends through the opening 210. FIG. 18 shows the splint or support of FIG. 17 in a formed three-dimensional configuration, with the opening 210 extending to the rear in the showing of FIG. 18. Thus, the construction of FIGS. 17 and 18 results in an inexpensive, simple, and effective splint or support. A thin layer of non-impregnated soft cloth material may be provided on the side of the double-knit material which is to engage the skin of the patient.

Relatively thin strips 207 and 209 of thermoplastic material may be folded over the upper edge and the thumb opening, respectively, and heat bonded to the double-knit type material, to protect the patient from the sharp edges which may be present in view of the high strength stiff fibers used in the support 202.

Now, referring back to FIG. 4 of the drawings, the dashed lines 172 represent a water vapor impermeable package for containing the orthopaedic product. This could be formed of metallized mylar, aluminum foil, or any known water vapor impermeable material, which will prevent premature activation and hardening of the urethane material which is impregnated into the double-knit material. One suitable water vapor proof sheet material involves aluminum foil, plastic coated on both sides, and is available from Richmond Tech, Inc., 1897 Colton Avenue, Redlands, Calif. 92374-9797. This material has a low moisture vapor transfer rate of about 0.0006 grams per 100 square inches per day. While the water-impermeable packaging is shown with regard to FIG. 4, it is also applicable to all of the other embodiments of the invention disclosed in this specification, following impregnation of the water-hardenable material.

For the products as described herein, the double-knit type material is initially impregnated with the water-hardenable urethane material, and then the entire soft good product, tape or blank, is packaged in the water vapor impermeable package. When it is time to apply the product to a patient, the package is opened, the product is immersed in water or water is applied to it; and the product is mounted onto the part of the anatomy requiring support or splinting. With the open-work matrix of the double-knit material, rapid and thorough penetration of the water and activation of the urethane occurs. In the case of the soft goods type of products, the straps are employed to mount the units firmly on the injured portion of the anatomy, water is applied or injected, and the water-hardenable material conforms to the configuration of the patient. Similarly, in the case of the blanks or the tapes, they are immersed in water and promptly applied to the injured portion of the anatomy before the hardening occurs.

Concerning the strength of the double-knit-type material as compared with several layers of fiberglass fabric, certain flexural modulus tests were done, with six inch by four inch samples. In the tests, the test samples were impregnated with the same water-hardenable material, were activated by water, and permitted to harden, with the same procedures being used for all samples. The test samples using the double-knit-type material weighed about 34 grams; and the weight of the fiberglass samples, using six layers of fiberglass, was about 40½ grams, or about 22% heavier than the double-knit-type material test samples. The strength of the double-knit-type samples was about 71 pounds at the yield point for the hardened samples, while the yield point for the layered fiberglass test samples was about 47 pounds. Accordingly, the double-knit-type material was nearly 50% stronger than the fiberglass samples, as well as being lighter.

Concerning the details of the test samples, the layered fiberglass samples were formed of six layers of Pinnacle Brand Fiberglass Tape. The double-knit-type material had fiberglass top and bottom layers, and the spacer yarn was monofilament plastic, 30 denier; and the fiberglass fabric had 23 courses and 14½ wales per inch, and was 446 denier. The six layers of fiberglass fabric together were about 0.20 to 0.25-inch thick, and the double-knit-type material was about 0.15-inch thick. Accordingly, the double-knit-type material was thinner, stronger and lighter weight than the conventional layered fiberglass casting material.

Figure 19:
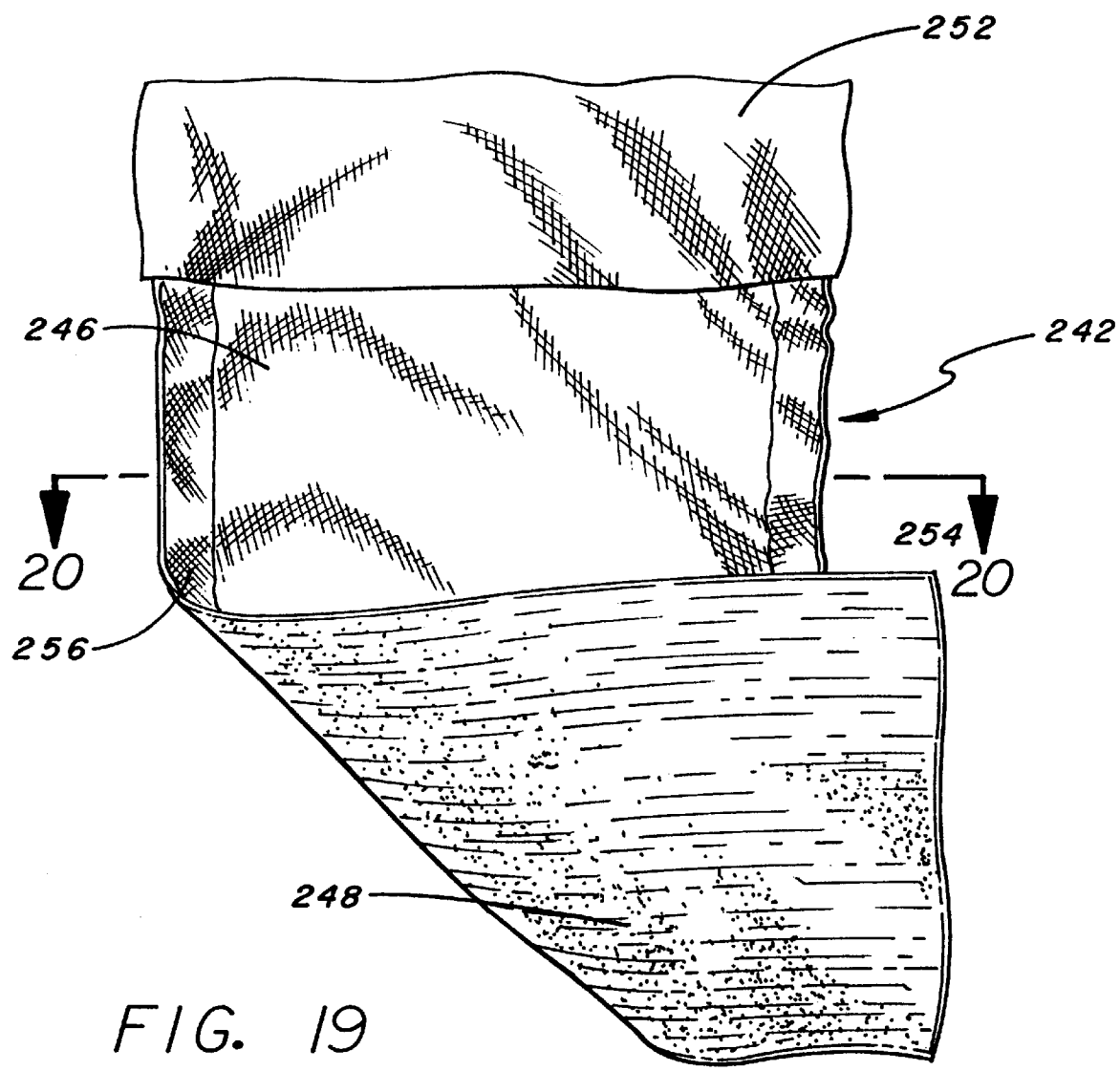
FIG. 19 shows an orthopaedic support or splint having a non-woven stretch bonded laminate on one side, and plastic sheet material with fine pores on the other side.
Figure 20:
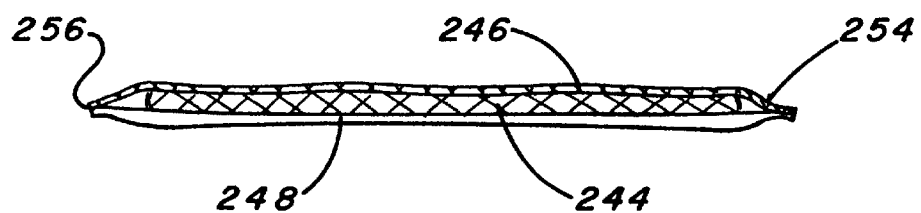
FIG. 20 is a cross-sectioned view taken along lines 20—20 of FIG. 19.

FIGS. 19 and 20 show an orthopaedic support or splint 242 which has an inner core or layer 244 of a double-knit type material, as shown for example in FIG. 1 of the drawings. The support or splint 242 has different materials on its two sides. On one side 246, it may have a very thin plastic layer having microperforations through which water may pass in order to harden the urethane hardening material impregnated into the central core 244. On the other side 248, the splint or support 242 may be provided with SBL type material or Stretch Bonded Laminate involving two non-woven layers which are bonded together by a water-resistant adhesive, so that the layer is essentially impermeable to water or moisture. This layer is intended for mounting adjacent the skin of a user. A suitable stretch bonded laminate material may be purchased from Kimberly Clark, 1400 Holcom Bridge Road, Roswell, Ga. 30076-2199. Other impermeable padding layers may be used, or water resistant padding may be employed.

Figure 21:
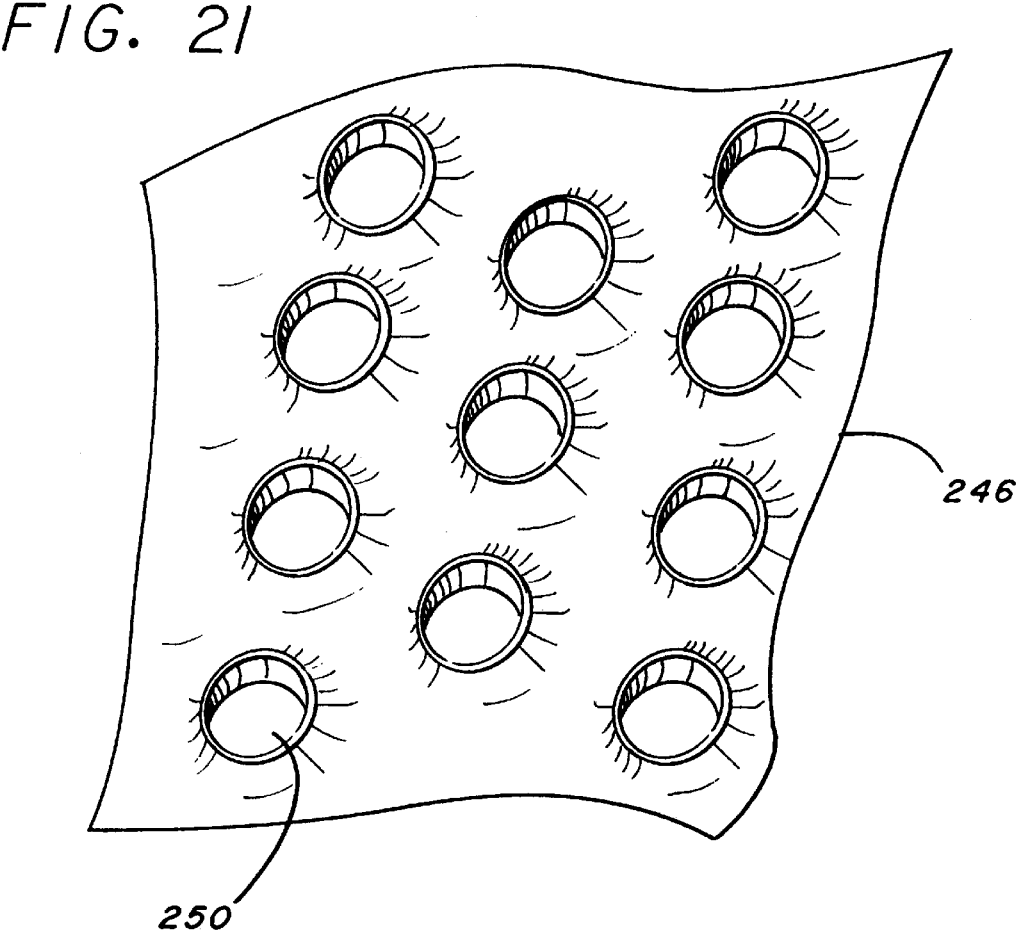
FIG. 21 is an enlarged perspective view showing the tapered openings in the plastic layer on one side of the assembly of FIG. 19.

As mentioned above, it is desirable that the central core 244 may be easily and thoroughly wetted at the time when the splint or support is to be used on a patient. This is accomplished by the use of any porous material, preferably porous plastic sheet material such as the micropore plastic layer 246 as shown in greater detail in FIG. 21. As shown in FIG. 21, the micropore penetrated thin plastic sheet 246 has a large number of closely spaced openings 250 which have side walls which are tapered in one direction for easy flow of water in that direction, and somewhat higher resistance to moisture or water flow in the opposite direction. Thus, with the lips of the micropores 250 being pointed inwardly toward the central core 244, wetting of this core is easily accomplished, and water does not tend to flow easily back out of the pores. While any thin porous material may be used, material sold under the trademark "VISPORE" is preferred, and it is available from Tredegar Film Products, 1100 Boulders Parkway, Richmond, Va. 23225. The VISPORE plastic film may be purchased with different numbers of holes per square inch, with some of the available sizes having from 88 to 1,840 holes per square inch. It is desirable to have more than 25 or 50 holes per square inch, but other hole sizes and numbers of holes per square inch permitting full wetting may be used. Fine plastic film with apertures, such as the VISPORE film, has a smooth silky feel and is very suitable for splints or braces which may be in contact with the user.

A thin pad 252 formed of any suitable padding material, such as plastic foam material or a soft thermoplastic fabric, may be folded over the ends of the double-knit type core material 244 at both ends thereof, and may be bonded to the ends in any suitable manner as by thermal bonding, by the use of adhesive, or in any other manner. This serves to cushion the ends of the splint, and keep them from irritating the patient at the points where the core ends. In addition, it will protect against any potential fraying of the ends of the core. This prevention of fraying is particularly helpful in cases where the double-knit or other core fabric is formed in whole or in part of fiberglass which otherwise may fray at locations where the fabric has been cut.

The two layers 246 and 248 may be bonded at their outer edges 254 and 256 by thermal welding, by permanent adhesive, by ultrasonic welding, or in any other desired manner. The bonding may be accomplished in successive spots or lines or may be continuous. Ultrasonic welding equipment is available from Branson Ultrasonics Corp., 41 Eagle Road, Danbury, Conn. 06813-1961.

Figure 22:
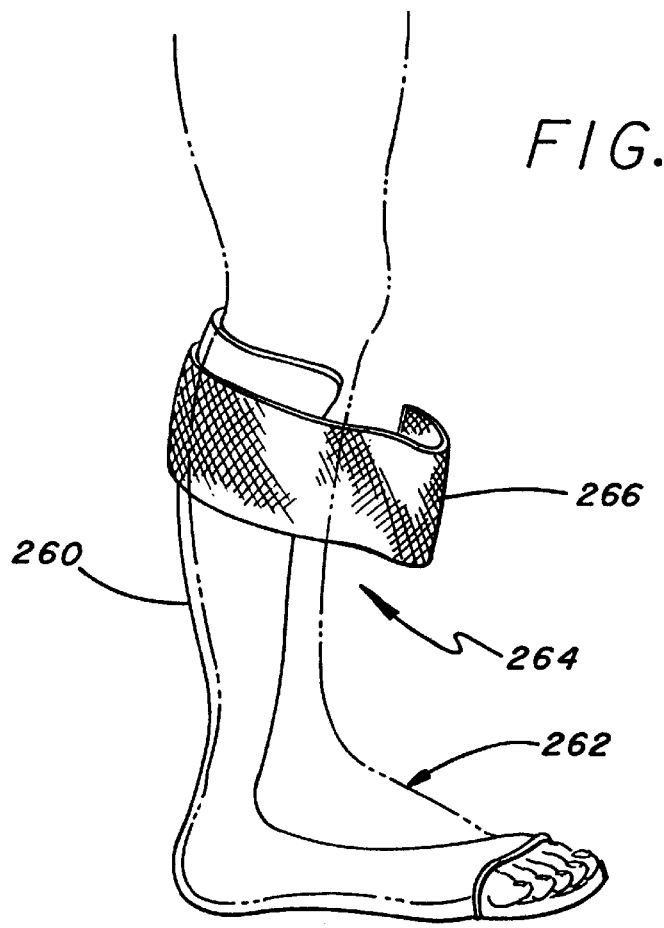
FIG. 22 shows an orthopaedic splint having different thicknesses, as employed on the lower leg and foot of a patient.
Figure 23:
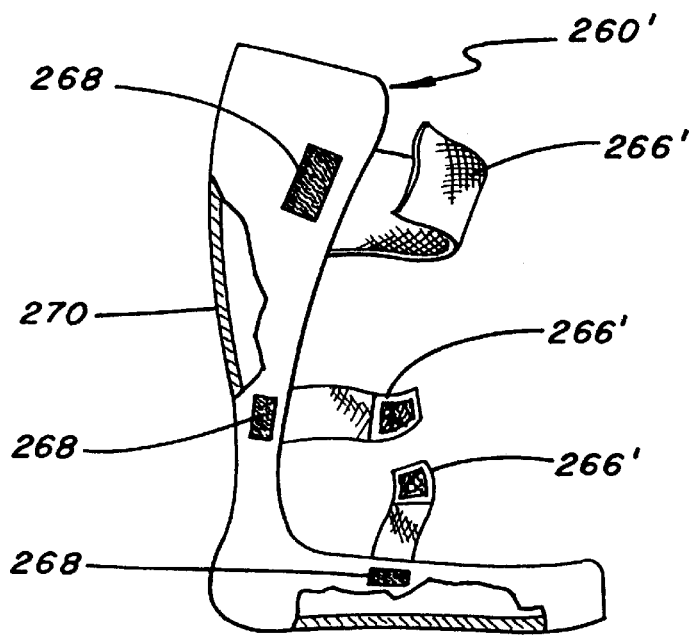
FIG. 23 shows an alternative embodiment of the splint in which the strap is formed integrally with the remainder of the splint.

Referring now to FIGS. 22 and 23, FIG. 22 shows a cast or support 260 mounted on the foot 262 and lower leg 264 of a patient. One strap 266 is shown for securing the cast or support in place. Additional straps may be provided at the instep and at the foot area. FIG. 23 shows a cast or support 260' which is similar to that shown in FIG. 22, but includes the straps 266' which are formed integrally with the double-knit type fabric forming the basic core of the brace or support or splint 260'. Incidentally, the knit material forming the core and straps of the brace shown in FIG. 22 may be of such construction that it includes loops of the type employed in VELCRO® type hook and loop fastening arrangement. The tabs 268 are mounted on the outer surface of the brace 260', and serve to secure the straps in place, when they are wrapped around the lower leg or foot of the patient.

It may also be noted that the support or splint 260' includes areas of different cross-sectional thickness, such as the relatively thin area 270 extending along the lower leg including the calf of the patient, as compared with the relatively thicker area 272 underlying the foot of the patient. As mentioned above, these varying thicknesses may be knit into double-knit type material by the machines manufactured by the German company, H. Stoll GmbH & Co. of Germany, with the address having been set forth hereinabove. Various complex knitted forms may be prepared as discussed herein, and in practice the exact desired size, shape and other specifications would be provided to the systems engineer/operator of a Stoll computer controlled machine, such as the Stoll CMS 340.6 knitting machine. The specifications would be encoded into a compatible Sirex pattern preparation system, which would control the knitting machine, to produce the specified product.

The straps 266' may be knit concurrently with the formation of the basic splint or support core material by suitably programming the machines. However, in some cases, it would be easier and more expeditious to provide separate straps, such as the strap 266 shown in FIG. 22 of the drawings. It is further noted that, instead of forming the splint or support 260 or 260' as a flat blank, it may be formed initially in a three-dimensional configuration, so that problems of wrinkling or overlapping cast areas may be avoided.

With further reference to FIG. 23, indicated schematically at reference numeral 273, is an outer layer of perforated plastic material such as the VISPORE material; and an inner layer 275 of padding such as the SBL material previously mentioned may be provided as a lining to the cast. Accordingly, this embodiment, and other embodiments of the invention, may benefit from the advantages of (1) double-knit type material generally, (2) a preformed three-dimensional knit or woven configuration, (3) edges which are closed knit so there are no frayed edges, (4) an inner lining which serves as padding and which may be waterproof, and (5) an outer protective lining which may be formed of perforated plastic sheet material.

Figure 24:
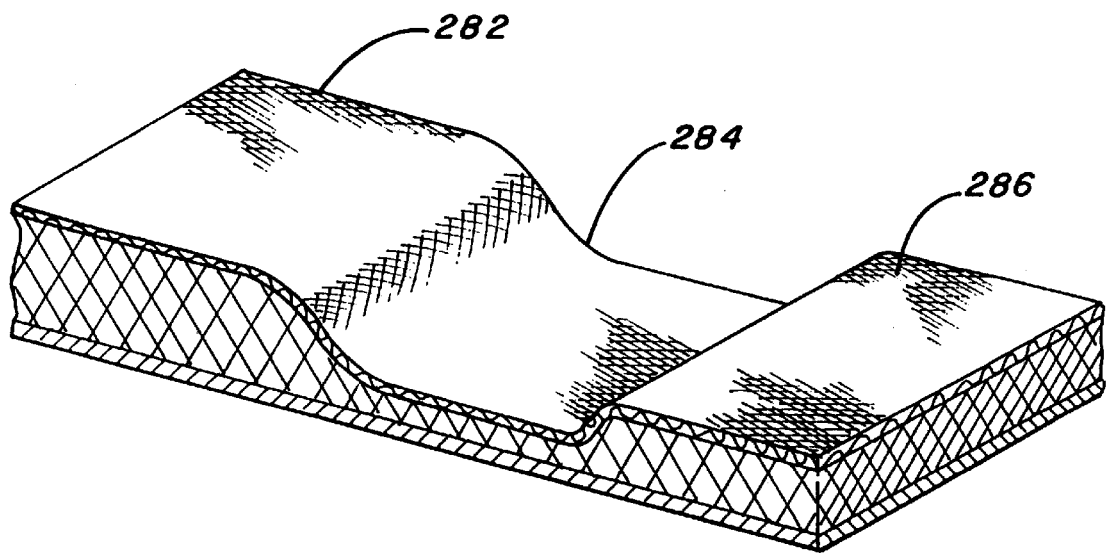
FIG. 24 illustrates a double-knit type material with varying thickness integrally knit into the fabric.

FIG. 24 is a generalized showing of a type of fabric material of the double-knit type which can be manufacturing in varying thickness lengths, with the thickness of the double-knit type material varying from a relatively thick portion as indicated at reference numeral 282, to a relatively thin configuration 284, and eventually to an intermediate thickness section of the double-knit type material at reference numeral 286.

Figure 25:
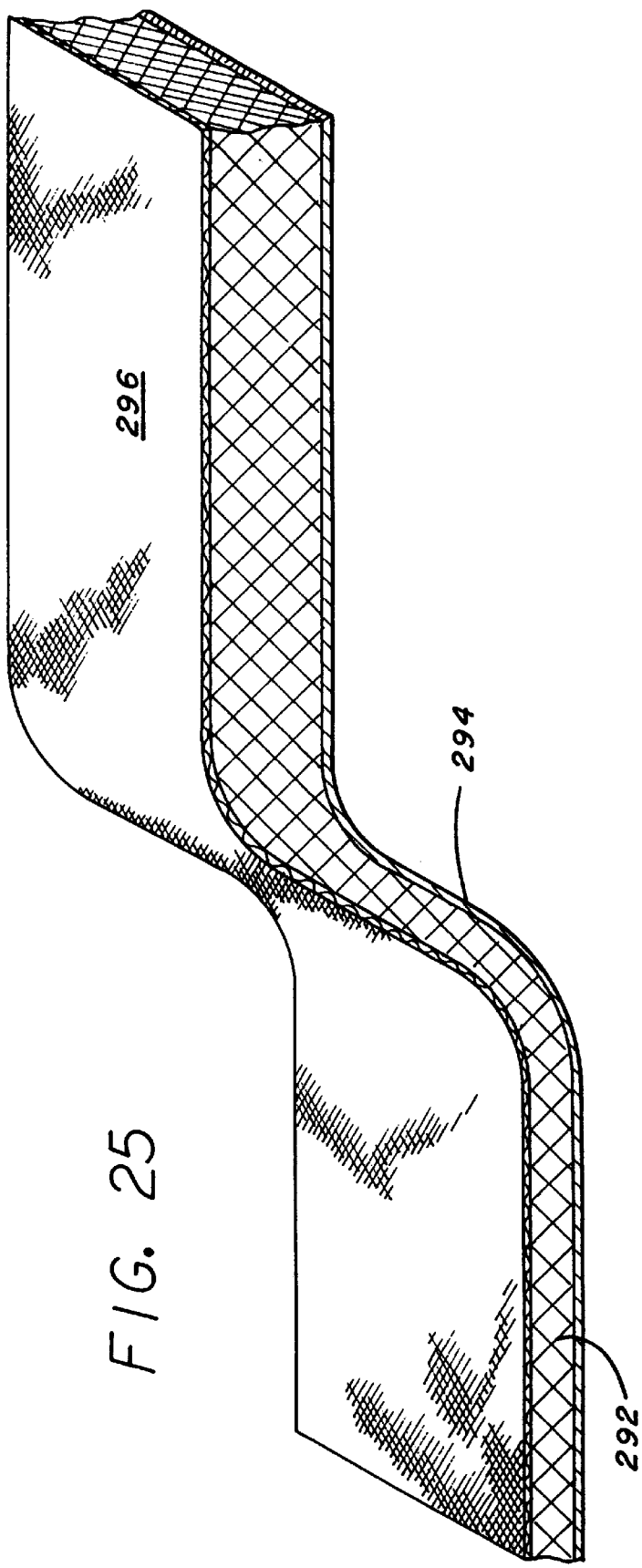
FIG. 25 is another showing of a variable knit construction having both a three-dimensional and a variable thickness configuration.

In addition, as shown in FIG. 25, the double-knit material may be formed in three dimensions, with a first portion 292 being relatively thin, and with an intermediate transitional portion 294 extending up out of the plane of the section 292, and then a third area 296 which is somewhat thicker and which extends in a plane parallel to the plane of section 292.

Figure 26:
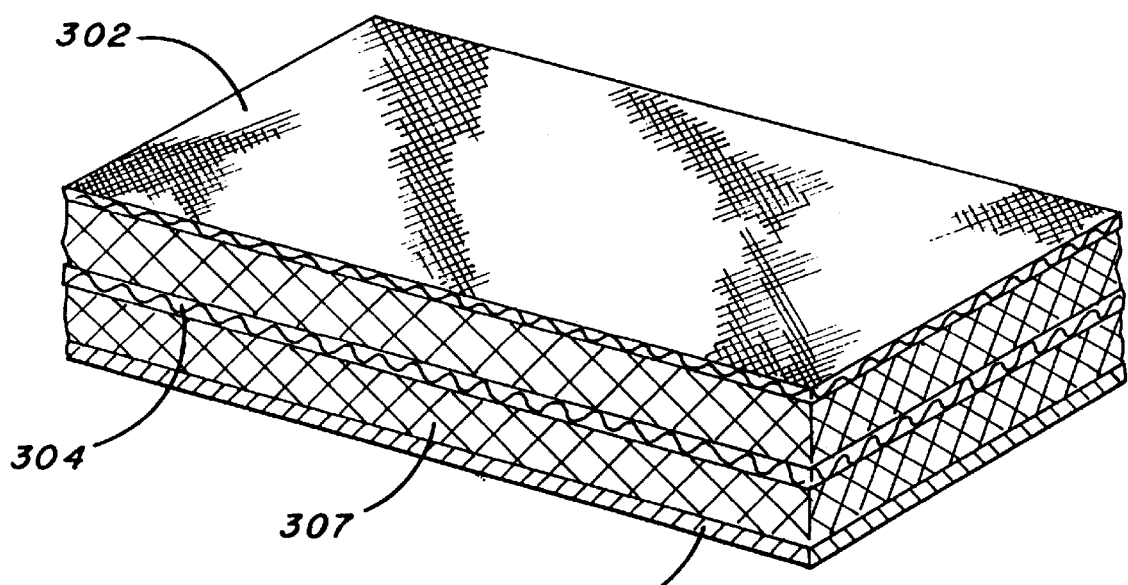
FIG. 26 shows a double-knit type material including an intermediate fabric layer as well as upper and lower outer layers.

FIG. 26 demonstrates still another alternative, in which the double-knit type material, or actually the triple-knit type material has three fabric layers, 302, 304 and 306, and intermediate strands or yarns 307 extending between layers 302 and 304, and between fabric layers 304 and 306. Alternatively, instead of the integral three layer arrangement as shown in FIG. 26, two assemblies each shown in FIG. 1 may be employed and bonded together in order to form a thicker, more cushioning layer of double-knit or triple-knit type material.

Figure 27:
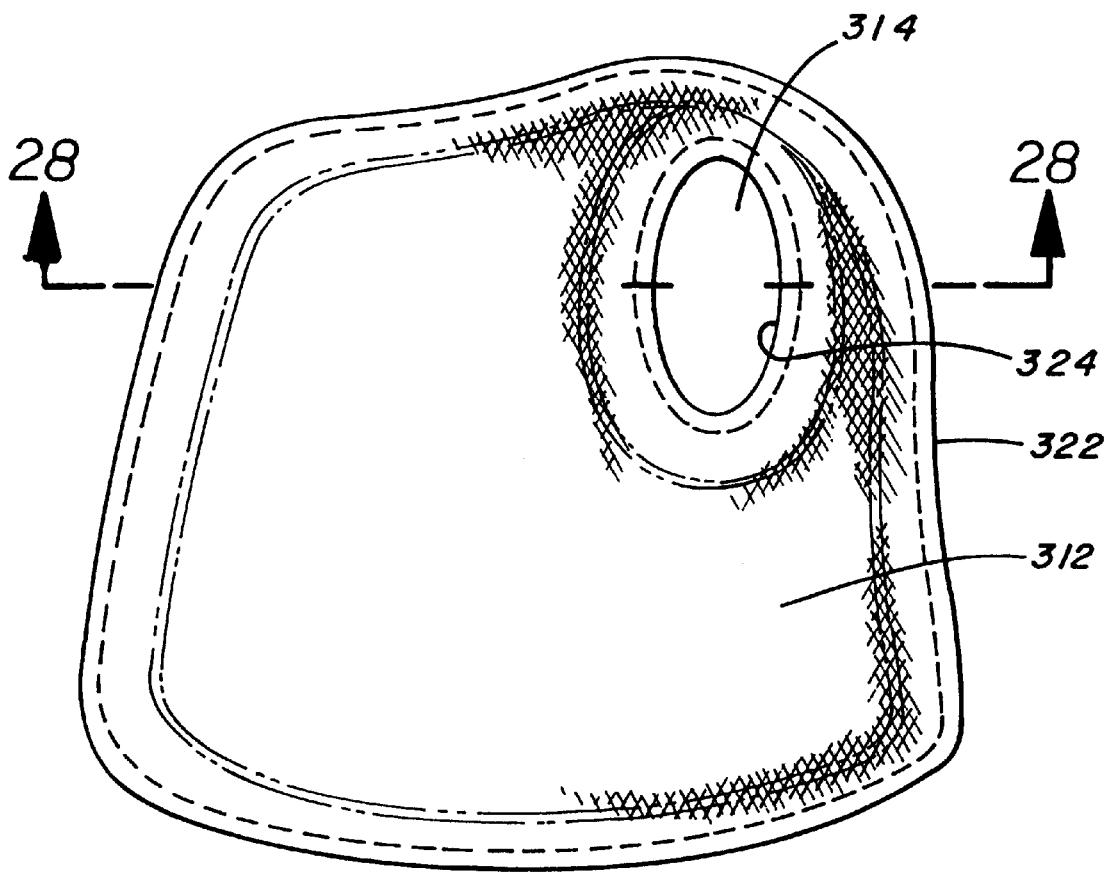
FIG. 27 shows a blank for forming a cast for the forearm.
Figure 28:
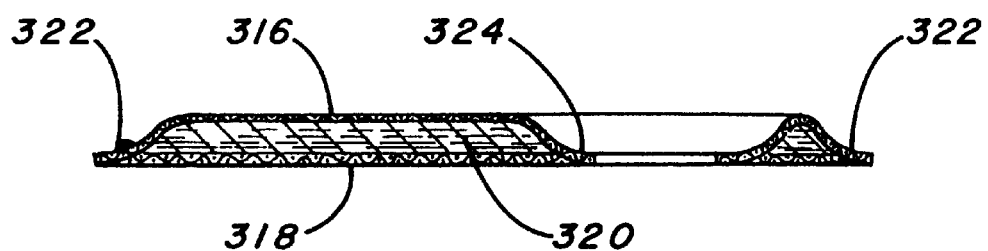
FIG. 28 is a cross-sectional view taken along lines 28—28 of FIG. 27.

Referring now to FIGS. 27 and 28 of the drawings, these figures show a blank 312 for forming a cast for the forearm, with the opening 314 being for the thumb of the patient. As is best shown in FIG. 28, the main portion of the blank 312 is formed of double-knit type material including an upper layer 316, a lower layer 318 and an intermediate layer or open-work matrix 320 of yarns or fibers extending between the upper and lower layers. At the edges 322 around the entire blank 312, and at the edges 324 around the thumb opening 314, the knit material is merged from two layers down to a single fabric layer, and the edges are knit in a closed manner so that there are no cut or frayed edges to unravel.

Figure 29:
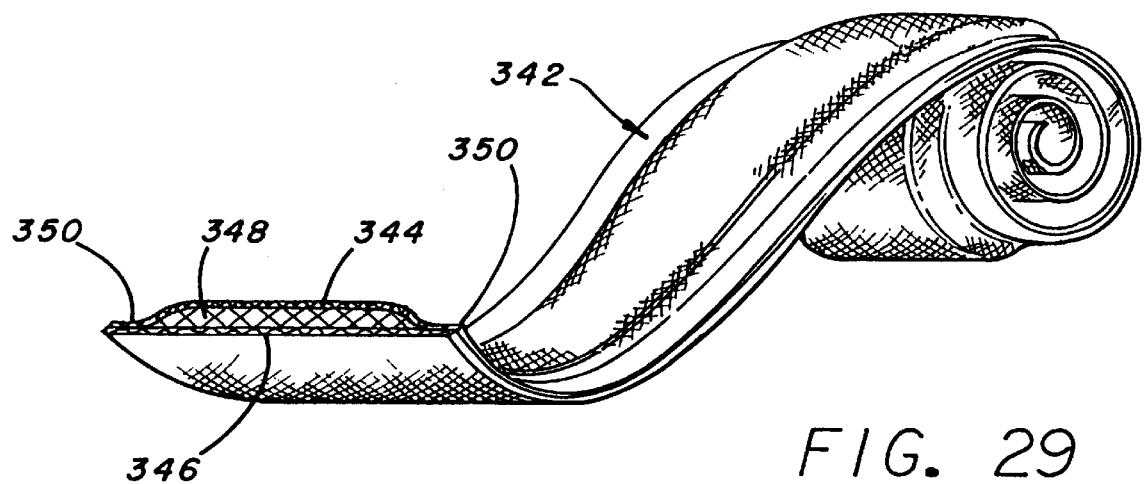
FIG. 29 shows a casting tape formed of double-knit type material tapering to closed knit lateral edges.

FIG. 29 is a perspective and diagrammatic showing of a casting tape 342 having a central area of double-knit type fabric, with an upper layer 344, a lower layer 346, and an intermediate open-work matrix 348 of yarns or fibers integrally knit or woven into the fabric and extending between the two layers. At the edges 350 of the tape, the two layers are merged into a single thickness of fabric, and it is a closed fabric with no loose edges to fray.

As in the case of other products described in this specification, the casting blank of FIGS. 27 and 28, and the casting tape of FIG. 29 are impregnated with water hardenable material, such as the urethane described elsewhere herein, and the products are packaged in moisture-proof packages.

Now, at the time when water is applied to any of the assemblies disclosed in this specification, it is important that the water freely and rapidly penetrates the double-knit type material where the water hardenable methane is located. This penetration may be facilitated by using a special knit pattern for the double-knit material with openings knit into the outer layer of the double-knit material, and with a smoother, even weave on the inner layer, as indicated schematically by the openings 115 as shown on one side of the tape 114 of FIG. 8, and the evenly woven layer 117 on the other side of the tape 114. In one sample double-knit material, the holes 115 were oval, and had a minor dimension of about 1/16-inch and a major or longer dimension of about 1/8-inch. Instead of the specially woven fabric with relatively large openings on one side (intended to be the outer side) only, the fabric may be formed with a relatively loose weave on one (outer) side and a tighter weave on the other (inner) side. Further, it is to be understood that this principle of having one layer more easily penetrable than the other layer, is applicable to all of the products disclosed in the present specification and drawings, and not just to FIG. 8.

Figure 30:
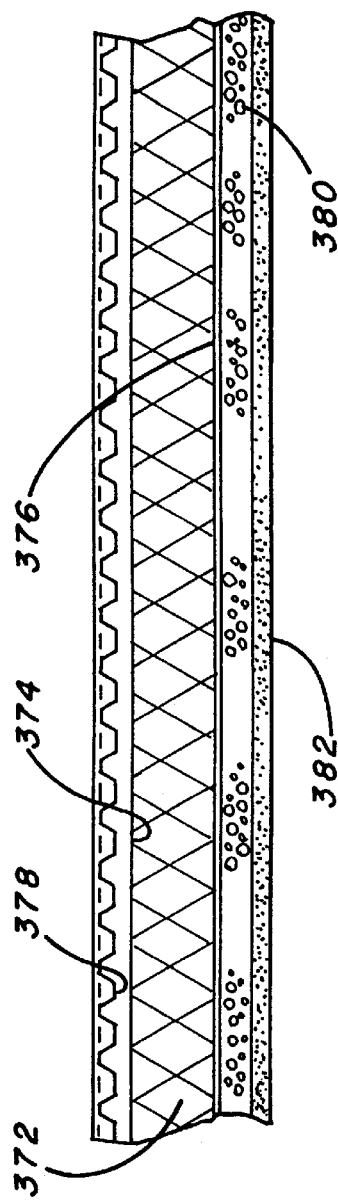
FIG. 30 is a schematic cross-sectional view of a splinting or casting layer including arrangements for facilitating water penetration.

Referring now to FIG. 30 of the drawings, it includes a central layer 372 of double-knit type material, with upper and lower layers 374 and 376. This double-knit type fabric 372 is impregnated with water hardenable material such as urethane. Upper our outer layer 378 may be formed of apertured plastic sheet material such as the VISPORE material mentioned hereinabove. Below the double-knit hydrophilic material, such as the known "super soaker" material; and below layer 380 is a padding layer 382 which may be water resistant or water impermeable material such as the SBL layer identified hereinabove. With this arrangement, the activating water flows through the apertured plastic layer 378 and through the double-knit material, freely penetrating and activating it, with the water flow enhanced by the presence of the lower hydrophilic layer 380.

Concerning another aspect of the assemblies disclosed herein, it is preferred that the double-knit type material include a substantial proportion of high strength materials such as fiberglass, aramid fibers such as Kevlar, or carbon fibers. In the following tables, the tensile strength of these high strength fibers are compared with other known lesser strength fibers.

TABLE NO. 1

Comparison of high strength fibers due to break strength
*Tensile strength -- the amount of force to break the fiber during elongation (Max Elongation)

| Material | Tensile Strength (MPa) | Tensile Strength (Psi) |
| --- | --- | --- |
| E Fiberglass | 1,400–2,500 | ~203,000—365,000 |
| Kevlar 29 | 3,600 | ~522,000 |
| Kevlar 49 | 3,600 | ~522,000 |
| Carbon fiber type 1 | 2,200 | ~320,000 |
| Carbon fiber type 2 | 2,700 | ~390,000 |
| Polyester | 45–85 | ~6,500—12,500 |
| Nylon | 60–110 | ~8,700—16,000 |
| Acrylics | 200–312 | ~30,000—45,000 |

MPA--Megapascal (kilonewtons per square meter)
Psi--Pounds per square inch

In the foregoing table, the tensile strength of the materials is given in both MPa and Psi, where MPa is short for Megapascal units (kilonewtons per square meter) and Psi stands for pounds per square inch.

It is noted that the high strength fibers, fiberglass, Kevlar and carbon fibers all have tensile strength which are an order of magnitude greater than the other known fibers. More generally, they have tensile strengths greater than 500 MPa, and preferably over 1,000 MPa. They are also fairly stiff; and in order to accommodate this associated stiffness, the double-knit type fabric is of a fairly loose weave, as mentioned hereinabove, to accommodate this fiber stiffness.

It is again noted that the formation of casting blanks and other orthopaedic supports with specially closed configurations at the edges, desired transitions from double- to single-knit or woven layers, as well as three-dimensional orthopaedic supports preshaped to fit on selected portions of the anatomy, may all be produced on special machines manufactured by Stoll GmbH, as discussed elsewhere in this specification.

It is to be understood that the foregoing detailed description and the accompanying drawings relate to preferred embodiments of the invention. Further modifications and variations of the present invention are contemplated, with products similar to double-knit material with two surface materials and intermediate spacer filaments or threads being specifically envisioned. Also, instead of stitching, heat bonding, or the use of adhesives may be employed to hold the parts or areas of the supports together. Also, in some cases, the outer channel 42 may be dispensed with, and the straps or other closure structures may be provided (see FIG. 17 for example), secured to edges of the layered material, or overlapping edges may be provided with VELCRO type material, or eyelets or hooks and laces, to hold the support in place.

With regard to materials which may be used, it is desired that one or both of the outer layers of the double-knit-type material be of high strength material, such as fiberglass, aramids such as kevlar, or other high strength fibers or materials. The spacer yarns, and one of the two outer layers may be formed of polypropylene, polyester, or nylon. Other materials and yarns may also be used. Concerning the thickness of the double-knit-type material, it may range from 1/16-inch thickness to 3/4-inch thickness, with 1/8-inch to 3/8-inch being preferred. For a finger splint, for example, relatively thin double-knit-type material would be used, while for a leg or ankle brace or support, much thicker material would be employed. It is further noted that the properties of the double-knit-type knit-type casting material may be changed as desired by (1) altering filament size of the surface yarns or spacer yarns, (2) changing the type of surface knits, (3) changing the density of spacer yarns, (4) interweaving stretchable yarns such as lycra to increase conformability and recovery, and (5) selectively inlaying high strength fibers such as carbon, kevlar or the like. It is also noted that flat or contoured casting blanks may be knit in a completed form so that the steps of cutting the material and securing against fraying may be avoided. In addition, hardenable material other than water-hardenable material may be employed in combination with an appropriate activating agent, with the combination being epoxy or other known two-part polymer hardening systems. Concerning the thickness of the double-knit type material, it may range from 1/32 of an inch up to 1/2-inch or even one inch in thickness depending on the conformability and strength which is required or desired.

It is further noted that construction discussed in connection with FIGS. 19 and 20, using impermeable padding on one side of the core material and flexible porous plastic on the other side is also applicable to the constructions shown elsewhere in the drawings. Thus, by way of example and not of limitation, the side of the embodiments to be facing the skin, as shown in FIGS. 6, 7, 8, 9, 13, 15, 16, 17, 18 and 22–26 may be of the impermeable padded material, and the opposite side of each splint or support may be formed of the flexible porous plastic material for ease in wetting the core material.

Similarly, all of the disclosed embodiments may be of variable thickness to provide selected areas of increased strength or of increased conformity to bodily configurations. It is also noted, with regard to the SBL material and the specific perforated flexible plastic, that the disclosed materials are preferred but that other materials providing substantially the same function may be used.

It is also noted that all of the embodiments of the invention may be provided with the moisture impermeable packaging 172 as indicated schematically in FIG. 4, and discussed hereinabove, to avoid hardening of the supports or splints prior to use, while in storage, on sale, or the like.

Accordingly, the present invention is not limited to the specific embodiments described hereinabove and shown in the drawings.

What is claimed is:

1. An orthopaedic method comprising the steps of:
    a) forming an integral double layer fabric having spaced interwoven layers formed of high strength filaments and an open-work matrix of filaments interconnecting said layers, said high strength filaments being selected from the group consisting of fiberglass, aramids, and carbon fibers, said fabric further including at least 20% by weight of thermoplastic fibers; said method including forming said integral double layer fabric including an upper layer and a lower layer and said open work matrix of filaments, in a single manufacturing step with said filaments being woven or knitted into both said upper and said lower layer, to space said layers apart;
    b) impregnating said open-work matrix of filaments with a water-hardenable material under low humidity conditions, while retaining the configuration of said matrix permeable to receive water;
    c) applying a water resistant layer of padding material to one side of said fabric and a layer of porous plastic on the other side thereof, to form a support assembly, said padding material having a cloth outer surface for engaging the skin;
    d) packaging said assembly in a water vapor impermeable package;
    e) subsequently opening said package;
    f) supplying water to said open-work matrix through said porous layer following opening of said package to rapidly wet said water-hardenable material; and
    g) locating the assembly including the impregnated double layer material adjacent the injured part of the anatomy so that said material conforms to the configuration of the anatomy, with the layer of padding material adjacent the skin;
    whereby the open-work matrix of said double layer fabric facilitates rapid and uniform impregnation by the water-hardenable material, and uniform penetration of the water, and also provides firm support resulting from the hardening of the water-hardenable material in the open-work matrix, and wherein the combination of high strength fibers and thermoplastic material permits concurrent cutting and heat bonding of the edges of the fabric.

2. A method as defined in claim 1 wherein said forming step includes forming said double layer fabric in varying thicknesses in a single manufacturing process with the varying thicknesses included in a single fabric.

3. A method as defined in claim 1 wherein said applying step includes applying padding material in the form of a stretch bonded laminate.

4. A method as defined in claim 1 wherein said applying step includes applying a layer of microporous plastic material having more than 50 pores or small openings per square inch.

5. A method as defined in claim 1 wherein said forming step includes initially knitting said fabric into a three-dimensional orthopaedic configuration corresponding to the part of the anatomy to be supported, and knitting said fabric into an orthopaedic support configuration with a closed knit configuration without severed fabric edges which might otherwise be subject to fraying.

6. A method as defined in claim 1 wherein the method includes forming the fabric as a double-knit type fabric having between 10 and 30 picks per inch and between 5 and 25 wales per inch.

7. A hardenable orthopaedic support assembly comprising a double layer fabric having a first interwoven layer and a second interwoven layer spaced apart from said first layer, and an open-work matrix of filaments interconnecting said layers; said fabric being formed in a manufacturing step with said filaments being woven or knitted into both of said two spaced layers;

said double layer fabric being impregnated with water-hardenable material leaving some space within said matrix to receive water;

a water resistant padding layer on one side of said double layer fabric;

a flexible porous layer on the other side of said double layer fabric;

said support assembly being fundamentally knit into a three-dimensional configuration generally conforming to a portion of the anatomy to be supported;

said fabric being knit into a closed knit configuration without severed fabric edges which might otherwise be subject to fraying; and said fabric being variable in thickness to provide an increased level of support in at least one area of said assembly.

8. A hardenable orthopaedic support assembly comprising:

a double layer fabric having spaced interwoven layers and an open-work matrix of fibers interconnecting said layers; said fabric being formed in a single manufacturing step with said filaments being woven or knitted into both of said two spaced layers;

said double layer fabric being impregnated with water-hardenable resin leaving some space within said matrix to receive water;

a water resistant fabric padding layer on one side of said double layer fabric; and a flexible porous layer on the other side of said double layer fabric;

whereby the open-work matrix of said double layer fabric and said porous layer facilitate rapid and uniform impregnation by the water-hardenable material, and rapid and uniform penetration of the water, and also provides firm support resulting from the hardening of the water-hardenable material in the open-work matrix.

9. An assembly as defined in claim 8 wherein said assembly includes at least one layer of fiberglass material extending along said double layer fabric.

10. An assembly as defined in claim 9 wherein said fiberglass layer forms at least one of the layers of fabric of said double layer fabric.

11. An assembly as defined in claim 8 further comprising water vapor impermeable packaging for enclosing said assembly, for preventing premature activation and hardening of said water-hardenable material during storage prior to intentional activation.

12. An assembly as defined in claim 8 wherein said flexible porous layer has more than 50 pores or openings per square inch.

13. An assembly as defined in claim 8 wherein said padding layer is formed of two non-woven layers held together by a water resistant adhesive.

14. An assembly as defined in claim 8 wherein said padding layer is a stretch bonded laminate.

15. An assembly as defined in claim 8 wherein said double layer fabric is variable in thickness.

16. A hardenable orthopaedic support assembly as defined in claim 8 wherein said fabric is formed of at least 10% of material selected from the group consisting of fiberglass, aramid fibers or carbon fibers.

17. A hardenable orthopaedic support assembly comprising:

a double layer fabric having spaced interwoven layers and an open-work matrix of filaments interconnecting said layers, said fabric being a double-knit type fabric having between 10 and 30 picks per inch and between 5 and 25 wales per inch; said fabric being formed in a single manufacturing step with said filaments being woven or knitted into both of said two spaced layers;

said double layer fabric being impregnated with water-hardenable resin leaving some space within said matrix to receive water;

a water resistant fabric padding layer on one side of said double layer fabric; and a flexible porous layer on the other side of said double layer fabric;

whereby the open-work matrix of said double layer fabric and said porous layer facilitate rapid and uniform impregnation by the water-hardenable material, and rapid and uniform penetration of the water, and also provides firm support resulting from the hardening of the water-hardenable material in the open-work matrix.

18. A hardenable orthopaedic support assembly comprising:

an active double layer fabric having spaced interwoven layers and an open-work matrix of filaments or fibers interconnecting said layers; said fabric being formed in a single manufacturing step with said filaments being woven or knitted into both of said two spaced layers;

at least ten percent (10%) of said fabric being formed of fibers having a tensile strength greater than 500 Mpa; and said active layer being impregnated with the water-hardenable material;

whereby the open-work matrix of said double layer fabric facilitates rapid and uniform impregnation by the water-hardenable material, and rapid and uniform penetration of the water, and also provides firm support resulting from the hardening of the water-hardenable material in the open-work matrix.

19. A hardenable orthopaedic support assembly comprising:

an active layer formed of a double layer fabric having spaced interwoven layers and an open-work matrix of filaments inter-connecting said layers; said fabric being formed in a single manufacturing step with said filaments being woven or knitted into both of said two spaced layers;

said active layer being impregnated with water-hardenable material;

said spaced layers being independently movable with respect to each other, within the limits of said interconnecting fibers, for case in three-dimensional draping around the anatomy;

a padding layer including water resistant material on one side of said double layer fabric;

a flexible porous layer on the other side of said double layer fabric; and a water vapor impermeable packaging enclosing said impregnated double layer fabric;

whereby the open-work matrix of said active double layer fabric facilitates rapid and uniform impregnation by the water-hardenable material, and subsequent uniform penetration of water, and also provides firm support resulting from the hardening of the water-hardenable material in the open-work matrix.

20. A hardenable orthopaedic support assembly as defined in claim 19 wherein said double layer fabric has an outer layer and an inner layer, and at least one of these layers is fiberglass material.

21. A hardenable orthopaedic support assembly comprising:

an active layer formed of a double layer fabric having spaced interwoven layers and an open-work matrix of filaments interconnecting said layers, at least 10 percent by weight of said fabric being formed of high strength, stiff filaments of a material selected from the group consisting of fiberglass, aramids and carbon; said fabric being formed in a single manufacturing step with said filaments being woven or knitted into both of said two spaced layers;

said active layer being impregnated with water hardenable material;

said spaced layers being independently movable with respect to each other, within the limits of said interconnecting filaments for ease in three dimensional draping around the anatomy; and a water vapor impermeable packaging enclosing said impregnated double layer fabric, whereby the open work matrix of said active double layer fabric facilitates rapid and uniform impregnation by the water hardenable material, and subsequent uniform penetration of water, and also provides firm support resulting from the hardening of the water hardenable material in the open work matrix.

22. A hardenable orthopaedic support assembly as defined in claim 21 wherein said fabric is a double-knit type fabric having between 10 and 30 picks per inch and between 5 and 25 wales per inch.

23. A support assembly as defined in claim 21 wherein said active layer has one extended area having a first constant thickness, and a second extended area having a significantly different constant thickness to provide increased support in selected areas of said assembly.

24. An assembly as defined in claim 21 wherein a water resistant padding layer is provided on one side of said active layer, and a flexible porous plastic layer is provided on the other side of said active layer.

25. A hardenable orthopaedic support assembly as defined in claim 21 wherein said fabric is a double-knit type fabric having between 18 and 28 picks per inch and between 10 and 20 wales per inch.

26. A hardenable orthopaedic support as defined in claim 21 wherein said fabric includes at least 20% by weight of thermoplastic filaments, whereby the edges of said fabric may be cut and heat bonded to avoid fraying of said high strength, stiff filaments.

27. A hardenable orthopaedic support or cast assembly comprising:

a high strength fabric core layer;

said fabric core layer being impregnated with water hardenable resin;

a water resistant fabric padding layer on one side of said fabric core layer for comfortable engagement with the skin of a patient; and the only material on the other side of said core layer consistency essentially of a thin flexible porous plastic layer for permitting wetting of said water hardenable material;

whereby the water resistant padding layer inhibits the flow of fluid from said fabric core layer to the patient, and said porous layer facilitates water flow to activate hardening of said core.

28. A hardenable orthopaedic support assembly comprising:

a double layer fabric having spaced interwoven layers and an open-work matrix of filaments interconnecting said layers; said fabric being formed in a single manufacturing step with said filaments being woven or knitted into both of said two spaced layers;

said double layer fabric being impregnated with water-hardenable material leaving some space within said matrix to receive water;

said support assembly being fundamentally knit into a three-dimensional configuration generally conforming to a portion of the anatomy to be supported;

said fabric being knit into a closed knit configuration without severed fabric edges which might otherwise be subject to fraying; and said fabric being variable in thickness to provide an increased level of support in at least one area of said assembly.

29. A hardenable orthopaedic support assembly comprising:

a high strength fabric core layer;

said fabric core layer being impregnated with water-hardenable material;

said support assembly being fundamentally knit into a three-dimensional configuration generally conforming to a portion of the anatomy to be supported; and said fabric being knit into a closed knit configuration without severed fabric edges which might otherwise be subject to fraying.

30. A method utilizing the orthopaedic support assembly as defined in claim 21 including the steps of opening the packaging and applying the double layer fabric to a portion of the anatomy of a patient requiring support.

31. A hardenable orthopaedic support assembly comprising:

a double layer fabric having first and second spaced interwoven layers and an open-work matrix of filaments interconnecting said layers; said fabric being formed in a single manufacturing step with said filaments being woven or knitted into both of said two spaced layers;

said double layer fabric being impregnated with water hardenable resin leaving some space within said matrix to receive water;

said first layer being relatively open for the transmission of water through said first layer; and said second layer being relatively closed as compared to said first layer, to restrict flow through said second layer;

whereby the open work matrix of said double layer fabric and the porous first layer facilitate rapid and uniform impregnation by the water hardenable material, and rapid and uniform penetration of the water, and the closed configuration of said second layer protects the patient from the effects of the exothermic hardening reaction.

32. A hardenable orthopaedic support assembly comprising:

a double layer fabric having spaced interwoven layers and an open-work matrix of filaments interconnecting said layers; said fabric being formed in a single manufacturing step with said filaments being woven or knitted into both of said two spaced layers;

said double layer fabric being impregnated with water hardenable resin leaving some space within said matrix to receive water;

said fabric being wound into a roll having a central core or mandrel upon which the fabric is wound; and water vapor impermeable packaging for enclosing said assembly, for preventing premature activation and hardening of said water hardenable material during storage prior to intentional activation.

33. A hardenable orthopaedic support assembly comprising:

a high strength double-knit type fabric core layer; said double knit type fabric core layer being formed with an upper layers a spaced lower layer, and intermediate filaments extending between and spacing said layers and woven or knitted into both of said layers;

said fabric core layer being impregnated with water-hardenable material; and said fabric being knit into a closed knit configuration without severed fabric edges which might otherwise be subject to fraying.

34. A method for forming a support or splint comprising the steps of:

forming a support assembly including a double-knit type fabric of a predetermined thickness, impregnated with a water hardenable resin; said double knit type fabric core layer being formed with an upper layer, a spaced lower layer, and intermediate filaments extending between and spacing said layers and woven or knitted into both of said layers;

packaging said assembly in a water vapor impermeable package;

opening said package;

applying water to said assembly to activate the exothermic hardening process;

molding said assembly to a portion of the anatomy requiring support while the assembly is still in the exothermic phase; and compressing some of the double-knit fabric so that it has different thicknesses in different areas, in the course of providing full support to the injured portion of the anatomy.

35. A hardenable orthopaedic support assembly comprising:

a double layer fabric having spaced interwoven layers and an open work matrix of filaments interconnecting said layers; said fabric being formed in a single manufacturing step with said filaments being woven or knitted into both of said two spaced layers;

said double layer fabric being impregnated with water hardenable resin leaving some space within said matrix to receive water;

a water resistant cloth padding layer on one side of said double layer fabric; and a layer of hydrophilic material between said double layer fabric and said water resistant layer to facilitate flow of water through said double layer material to activate said water hardenable resin.

36. A hardenable orthopaedic support assembly comprising:

a double layer fabric having spaced interwoven layers and an open-work matrix of filaments interconnecting said layers; said fabric being formed in a single manufacturing step with said filaments being woven or knitted into both of said two spaced layers;

said fabric being a double-knit type fabric having between 10 and 30 picks per inch and between 5 and 25 wales per inch, at least ten percent (10%) of said fabric being formed of fibers having a tensile strength greater than 500 MPa; and said double layer fabric being impregnated with water-hardenable resin leaving some space within said matrix to receive water;

whereby the open-work matrix of said double layer fabric facilitate rapid and uniform impregnation by the water-hardenable material, and rapid and uniform penetration of the water, and also provides firm support resulting from the hardening of the water-hardenable material in the open-work matrix.

37. A hardenable orthopaedic support assembly comprising:

a double layer fabric having spaced interwoven layers and an open-work matrix of filaments interconnecting said layers; said fabric being formed in a single manufacturing step with said filaments being woven or knitted into both of said two spaced layers;

said double layer fabric being impregnated with water-hardenable material leaving some space within said matrix to receive water;

said support assembly being fundamentally knit into a three-dimensional configuration generally conforming to a portion of the anatomy to be supported; and said fabric being variable in thickness to provide an increased level of support in at least one area of said assembly.

38. A hardenable orthopaedic support assembly comprising:

a double layer fabric having spaced interwoven layers and an open-work matrix of fibers interconnecting said layers, at least ten percent (10%) of said fabric being formed of fibers having a tensile strength greater than 500 MPa; said fabric being formed in a single manufacturing step with said filaments being woven or knitted into both of said two spaced layers;

said assembly being a flat sheet preformed into an anatomical shape for mounting on specific portions of the anatomy; and said double layer fabric being impregnated with water-hardenable resin leaving some space within said matrix to receive water;

whereby the open-work matrix of said double layer fabric facilitate rapid and uniform impregnation by the water-hardenable material, and rapid and uniform penetration of the water, and also provides firm support resulting from the hardening of the water-hardenable material in the open-work matrix.

39. A hardenable orthopaedic support assembly as defined in claim 38 wherein said assembly includes a closure structure for mounting said assembly on a portion of the anatomy.

40. A hardenable orthopaedic support assembly as defined in claim 39 wherein said closure structure includes straps.

* * * * *